(12) United States Patent
Hone

(10) Patent No.: US 7,018,835 B2
(45) Date of Patent: Mar. 28, 2006

(54) RECOMBINANT DOUBLE-STRANDED RNA PHAGE, AND USE OF THE SAME

(76) Inventor: David Michael Hone, 14708 Waterway Dr., Rockville, MD (US) 20850

( * ) Notice: Subject to any disclaimer, the term of this patent is extended or adjusted under 35 U.S.C. 154(b) by 219 days.

(21) Appl. No.: 10/632,094

(22) Filed: Aug. 1, 2003

(65) Prior Publication Data

US 2004/0132678 A1   Jul. 8, 2004

Related U.S. Application Data

(60) Provisional application No. 60/404,806, filed on Aug. 20, 2002.

(51) Int. Cl.
*C12N 15/79* (2006.01)
*C12N 15/63* (2006.01)
*C12N 15/86* (2006.01)

(52) U.S. Cl. .................. 435/320.1; 435/69.1; 536/23.1; 536/23.72; 424/93.1; 424/93.2; 424/93.6

(58) Field of Classification Search .................... None
See application file for complete search history.

(56) References Cited

OTHER PUBLICATIONS

Poranen, Virus Research, 2004, vol. 101, pp. 93-100.*
Mindich et al., J. Bacteriology, 1999, vol. 181, No. 15, pp. 4505-4508.*
Mindich, Microbiology and Molecular Biology Reviews, 1999, vol. 63, No. 1, pp. 149-160.*

* cited by examiner

*Primary Examiner*—David Guzo
(74) *Attorney, Agent, or Firm*—Whitham, Curtis, & Christofferson, PC

(57) ABSTRACT

A recombinant double stranded RNA (dsRNA) phage expresses dsRNA-encoded genes in eukaryote cells. Recombinant dsRNA phage are useful for the expression of dsRNA expression cassettes encoding passenger genes, such as, but not restricted to, vaccine antigens, bioactive proteins, immunoregulatory proteins, antisense RNAs, and catalytic RNAs in eukaryotic cells or tissues. Methods are provided to deliver recombinant dsRNA phage to eukaryotic cells and tissues, either by direct administration, formulated in lipid or polylactide-coglycolide, or by utilizing a bacterial vaccine vector.

20 Claims, 6 Drawing Sheets

Figure 1:
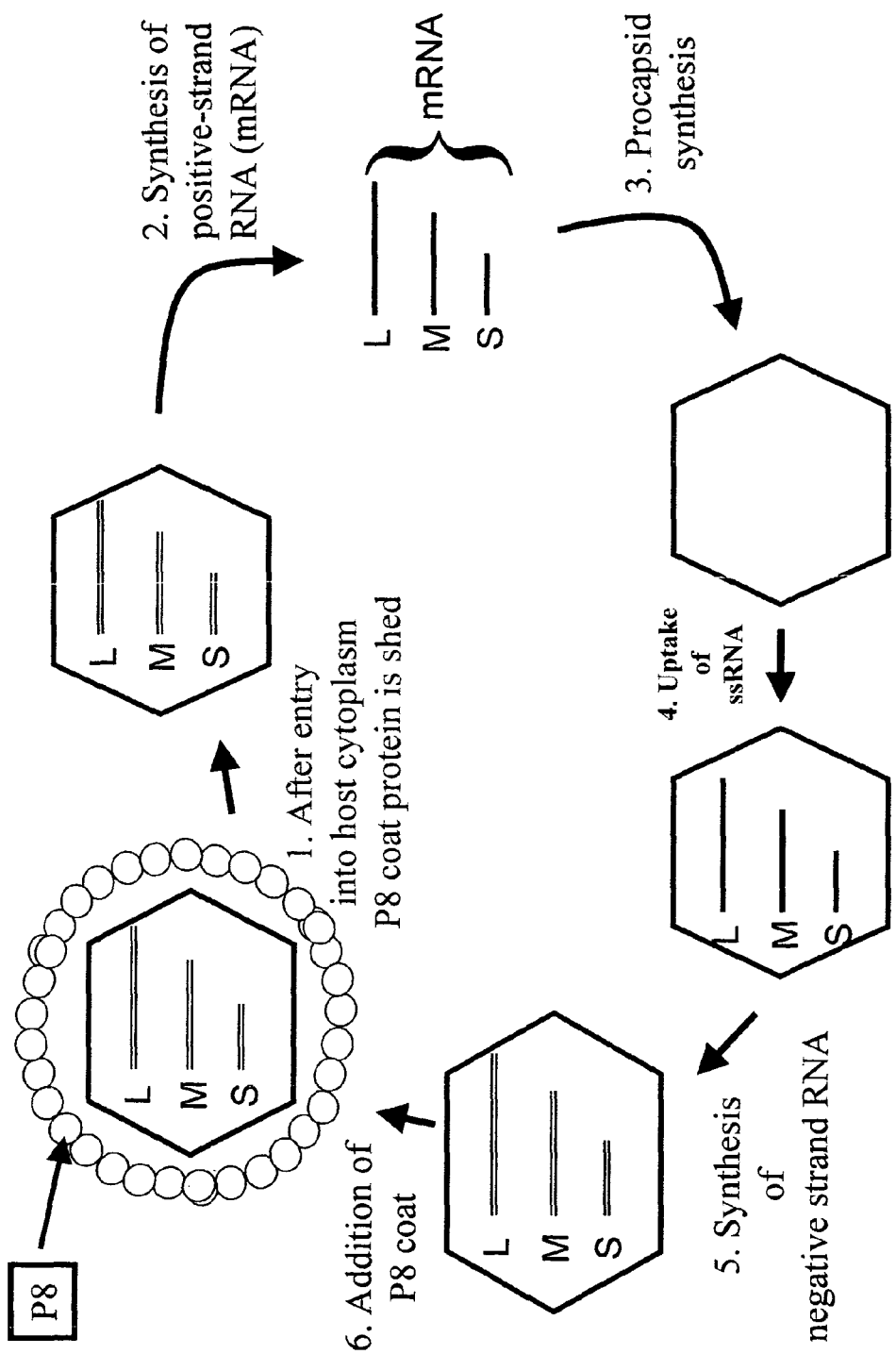

Replication of dsRP nucleocapsids in the bacterial cytoplasm

Cloning cDNA copies of the mRNA produced by dsRP

Construction of recombinant dsRP segments using cDNA clones

Generation of recombinant dsRP nucleocapsids

Figure 5

Schematic representation of rdsRP-1 segment-S

Arrangement of the recombinant segment-S in a self-amplifying rdsRP

RECOMBINANT DOUBLE-STRANDED RNA PHAGE, AND USE OF THE SAME

This application claims priority to U.S. Provisional Patent Application No. 60/404,806 filed on Aug. 20, 2002. The complete contents of that application are herein incorporated by reference.

This invention was made with the support of a grant from the National Institutes of Health (NIH) grant numbers R01-A14194 and R01-055367. The U.S. government has certain rights in this invention.

FIELD OF INVENTION

The present invention provides recombinant double stranded RNA (dsRNA) phage that express dsRNA-encoded genes in eukaryote cells. Recombinant dsRNA phage are useful for the expression of dsRNA expression cassettes encoding passenger genes, such as, but not restricted to, vaccine antigens, bioactive proteins, immunoregulatory proteins, antisense RNAs, and catalytic RNAs in eukaryotic cells or tissues. Methods are provided to deliver recombinant dsRNA phage to eukaryotic cells and tissues, either by direct administration, formulated in lipid or polylactide-coglycolide, or by utilizing a bacterial vaccine vector.

BACKGROUND

Double Stranded Ribonucleic Acid Phage

Double stranded RNA phage (herein "dsRP") are atypical compared to other RNA and DNA phage, and more closely resemble members of the reoviridae family [1–5]. The distinguishing attributes of dsRP are a genome comprised of three double-stranded RNA (herein "dsRNA") segments [2–4,6] and a lipid-containing membrane coat [7–12].

The genomic segments are contained within the nucleocapsid core, which is comprised of the proteins P1, P2, P4, and P7, and is produced by genes encoded on the 7051 bp dsRNA segment, designated "segment L" (GeneBank Accession # AF226851). Synthesis of positive-strand RNA (herein "mRNA") occurs within the nucleocapsid, which is carried out by RNA-dependent RNA polymerase that may be encoded by gene 2 on segment L, based on sequence similarity to other bacterial RNA polymerases [4,13]. However, gene 7 on segment L also plays a pivotal role in mRNA synthesis [5].

DsRP phi-6, the archetype of this family of dsRNA phage, normally infects *Pseudomonas syringae* [5], however, more recently isolated dsRP phi-8, phi-11, phi-12 and phi-13 can replicate to some extent in *Escherichia coli* strain JM109 (American type tissue culture collection (herein "ATCC") # 53323) and O-antigen negative mutants of *Salmonella enterica* serovar *Typhimurium* (herein designated "*S. typhimurium*") [5,14–16].

By inserting a kanamycin-resistance allele into the M-segment of a dsRP, carrier strains were established and maintained [17]. Through this approach, several of the dsRPs were found to be capable of establishing a carrier state in host cells, in which infectious phage are continuously produced by the carrier strain [17]. The plaque-forming capacity of the phage produced by the carrier strains is maintained for three-five plate passages; however, after additional passages the nascent phage no longer formed plaques on the carrier strain, yet low-levels of infectious phage were still produced [17]. In some instances, a significant number of carrier strains lost the ability to produce infectious phage all together, yet phage dsRNA segments were continuously maintained in the cytosol of such carrier bacteria. The dsRNA from such bacterial strains displayed deletions in one or more of the segments [17]. In one instance a mutant phage lacking the segment-S was isolated from one such carrier strain that had lost the capacity to produce phage [17,18].

The life cycle of the dsRP phi-6 in bacteria has been described [5,11]. Archetype dsRP phi-6 infects host cells by binding to the pilus. The phage then uses the pilus to allow contact with the host cell membrane, thereby resulting in fusion and introduction of the nucleocapsid into the periplasm. The nucleocapsid then is transported into the cytoplasm, an event that requires the endopeptidase activity of protein P5 and the transporting property of protein P8. Interestingly, nucleocapsids that bear a complete P8 shell are capable of spontaneous entry into bacterial protoplasts, resulting in auto-transfection of the bacterial strain from which the protoplasts were prepared [19,20].

Upon entering the cytoplasm, P8 is shed and the remaining nucleocapsid, which contains the three dsRNA segments and possesses RNA-dependent RNA polymerase activity, begins to synthesize mRNA copies of the dsRNA segments L, M and S (FIG. 1). The proteins produced by segment L are mainly associated with procapsid production; segment M is mainly dedicated to the synthesis of the attachment proteins and the segment S produces the procapsid shell protein (P8), the lytic endopeptidase (P5), and the proteins (P9 and P12) involved in the generation of the lipid envelope [12] (FIG. 1). Packaging of the dsRNA segments occurs in sequential manner, whereby segment S is recognized and taken up by empty procapsids; procapsids containing segment S no longer binds this segment but now are capable of binding and taking up segment M; procapsids that contain segments S and M no longer bind these segments but now are capable of binding and taking up segment L, resulting in the generation of the nucleocapsid. Once the nucleocapsid contains all three single-stranded RNA (herein "ssRNA") segments synthesis of the negative RNA strands begins to produce the dsRNA segments. The nucleocapsid then associates with proteins 5 and 8 (FIG. 1) and finally is encapsulated in the lipid membrane, resulting the completion of phage assembly. Lysis of the host cell is thought to occur through the accumulation of the membrane disrupter protein P10, a product of segment M and requires the endopeptidase P5 [5].

The assembly of and RNA polymerase activity in dsRP procapsids does not require host proteins, as procapsids purified from an *E. coli* JM109 derivative that expressed a cDNA copy of segment L are capable of packaging purified ssRNA segments L, M and S [5,19–24]. Following uptake of the ssRNA segments in the above in vitro system, addition of ribonucleotides resulted in negative strand synthesis and the generation of the mature dsRNA segments [5,19–24]. Furthermore, after the completion of dsRNA synthesis P8 associates with nucleocapsids and as indicated above the resultant product is capable of entering bacterial protoplasts and producing a productive infection [19,20].

Introduction of Nucleic Acids into Eukaryotic Cells

There are several techniques for introducing nucleic acids into eukaryotic cells cultured in vitro. These include chemical methods (Felgner et al, *Proc. Natl. Acad. Sci., USA*, 84:7413–7417 (1987); Bothwell et al, *Methods for Cloning and Analysis of Eukaryotic Genes*, Eds., Jones and Bartlett Publishers Inc., Boston, Mass. (1990), Ausubel et al, *Short*

Protocols in Molecular Biology, John Wiley and Sons, New York, N.Y. (1992); and Farhood, Annal. N.Y. Acad. Sci., 716:23–34 (1994)), use of protoplasts (Bothwell, supra) or electrical pulses (Vatteroni et al, Mutn. Res., 291:163–169 (1993); Sabelnikov, Prog. Biophys. Mol. Biol, 62: 119–152 (1994); Brothwell et al, supra; and Ausubel et al, supra), use of attenuated viruses [25–34](Moss, Dev. Biol. Stan., 82:55–63 (1994); and Brothwell et al, supra), as well as physical methods (Fynan et al, supra; Johnston et al, Meth. Cell Biol, 43(Pt A):353–365 (1994); Brothwell et al, supra; and Ausubel et al, supra).

Successful delivery of nucleic acids to animal tissue has been achieved by cationic liposomes (Watanabe et al, Mol. Reprod. Dev., 38:268–274 (1994)), direct injection of naked DNA or RNA into animal muscle tissue (Robinson et al, Vacc., 11:957–960 (1993); Hoffman et al, Vacc. 12:1529–1533; (1994); Xiang et al, Virol., 199:132–140 (1994); Webster et al, Vacc., 12:1495–1498 (1994); Davis et al, Vacc., 12:1503–1509 (1994); and Davis et al, Hum. Molec. Gen., 2:1847–1851 (1993); [35,36]), and embryos (Naito et al, Mol. Reprod. Dev., 39:153–161 (1994); and Burdon et al, Mol. Reprod. Dev., 33:436–442 (1992)), intramuscular injection of self replicating RNA vaccines [25–28, 35,36] or intradermal injection of DNA using "gene gun" technology (Johnston et al, supra).

Translation of mRNA into Protein in Eukaryotes and Prokaryotes

The ribosomal binding site (herein "RBS") is the site recognized by the ribosome for binding to the 5-prime (herein designated "5'") end of mRNA) molecules. This binding is essential for the translation of mRNA into a protein by the ribosome. In prokaryotes, a defined RBS in the 5' end of the mRNA molecule that bears a sequence that is complementary to the 3' end of the small ribosomal RNA molecule (5S rRNA) (Chatteji et al, Ind. J. Biochem. Biophys., 29:128–134 (1992); and Darnell et al, supra; Lewin, supra; Watson et al, supra; and Watson et al, supra). Thus, in prokaryotes the RBS promotes association of the ribosome with the 5' end of the nascent mRNA molecule, whereupon translation is initiated at the first initiation codon encountered (i.e. normally the methionine codon AUG) by the mRNA-associated ribosome (Darnell et al, supra; Lewin, supra; Watson et al, supra; and Alberts et al, supra). At present, no such recognition pattern has been observed in the 5' eukaryotic mRNA-ribosome interactions (Eick et al, supra). In addition, prior to initiation of translation of eukaryotic mRNA, the 5' end of the mRNA molecule is "capped" by addition of methylated guanylate to the first mRNA nucleotide residue (Darnell et al, supra; Lewin, supra; Watson et al, supra; and Alberts et al, supra). It has been proposed that recognition of the translational start site in mRNA by the eukaryotic ribosomes involves recognition of the cap, followed by binding to specific sequences surrounding the initiation codon on the mRNA. It is possible for cap independent translation initiation to occur and/or to place multiple eukaryotic coding sequences within a eukaryotic expression cassette if a internal ribosome entry site (herein "IRES") sequence, such as the cap-independent translation enhancer (herein designated "CITE") derived from encephalomyocarditis virus (Duke et al, J. Virol., 66:1602–1609 (1992)), is included prior to, or between, the coding regions. However, the initiating AUG codon is not necessarily the first AUG codon encountered by the ribosome (Louis et al, Molec. Biol. Rep., 13:103–115 (1988); and Voorma et al, Molec. Biol. Rep., 19:139–145 (1994); Lewin, supra; Watson et al, supra; and Alberts et al, supra). Thus, RBS sequences in eukaryotes are sufficiently divergent from that of prokaryotic RBS such that the two are not interchangeable.

Delivery of Nucleic Acids to Eukaryotic Cells

The commercial application of nucleic acid delivery technology to eukaryotic cells is broad and includes delivery of vaccine antigens (Fynan et al, Proc. Natl. Acad. Sci., USA, 90:11478–11482 (1993)), immunotherapeutic agents, and bioactive proteins designed to remedy genetic disorders (Darris et al, Cancer, 74(3 Suppl.):1021–1025 (1994); Magrath, Ann. Oncol., 5(Suppl 1):67–70 (1994); Milligan et al, Ann. NY Acad. Sci., 716:228–241 (1994); Schreier, Pharma. Acta Helv., 68:145–159 (1994); Cech, Biochem. Soc. Trans., 21:229–234 (1993); Cech, Gene, 135:33–36 (1993); Long et al, FASEB J., 7:25–30 (1993); and Rosi et al, Pharm. Therap., 50:245–254 1991)).

The delivery of nucleic acids to animal tissue for gene therapy has shown significant promise in experimental animals and volunteers, particularly where a transient effect is required (Nabel, Circulation, 91:541–548 (1995); Coovert et al, Curr. Opin. Neuro., 7:463–470 (1994); Foa, Bill. Clin. Haemat., 7:421–434 (1994); Bowers et al, J. Am. Diet. Assoc., 95:53–59 (1995); Perales et al, Eur. J. Biochem., 226:255–266 (1994); Danko et al, Vacc., 12:1499–1502 (1994); Conry et al, Canc. Res., 54:1164–1168 (1994); and Smith, J. Hemat., 1:155–166 (1992)). Recently, naked DNA vaccines carrying eukaryotic expression cassettes have been used to successfully immunize against influenza both in chickens (Robinson et al, supra) and ferrets (Webster et al, Vacc., 12:1495–1498 (1994)); against Plasmodium yoelii in mice (Hoffman et al, supra); against rabies in mice (Xiang et al, supra); against human carcinoembryonic antigen in nice (Conry et al, supra) and against hepatitis B in mice (Davis et al, supra). These observations open the additional possibility that delivery of nucleic acids to eukaryotic tissue could be used for both prophylactic and therapeutic applications, wherein the prophylactic application has a significant impact in the mortality and/or morbidity of the infectious agent, autoimmune disease or tumor prior to the acquisition of overt clinical disease, and the therapeutic application has a significant impact in the mortality and/or morbidity of the infectious agent, autoimmune disease or tumor following the development of overt clinical disease.

Therefore, there is a need to deliver eukaryotic expression cassettes, encoding endogenous or foreign genes that are vaccines or therapeutic agents to eukaryotic cells or tissue.

SUMMARY OF THE INVENTION

The present invention describes a novel and unexpected finding that dsRP are capable of delivering dsRNA eukaryotic expression cassettes to eukaryotic cells and tissue.

Heretofore, there has been no documented demonstration of dsRP invading eukaryotic cells and introducing a eukaryotic expression cassette(s), which then is translated by the infected cells and progeny thereof. That is, the present invention provides the first documentation of functional genetic exchange between dsRP and eukaryotic cells.

This invention provides recombinant dsRP that express dsRNA-encoded genes in eukaryote cells encoding a functional eukaryotic translation expression cassettes. The prior art teaches the biology of dsRP in prokaryotic cells, such as P. syringae, E. coli, and S. typhimurium. The mRNAs produced by dsRP are poorly translated in eukaryotic cells.

Surprisingly, we found that the incorporation of cap-independent eukaryotic translation, herein referred to as "CITE" (also known as an internal ribosome entry site, herein referred to as "IRES") sequences into dsRP enables expression in eukaryotic cells or tissues. CITE sequences are discussed in detail in U.S. Pat. No. 6,500,419 to Hone, and the complete contents thereof is herein incorporated by reference. As will be shown in more detail below the IRES sequence and a passenger gene of interest can be inserted into one or more of the three dsRNA segments in the dsRP [17]. The resultant recombinant dsRP carrying a recombinant segment or segments produces messenger RNA in eukaryotic cells that is recognized by the eukaryotic translation apparatus (See example below). The ensuing translation by the eukaryotic cell ribosomes results in the expression of the passenger gene of interest.

Another object of this invention describes recombinant dsRP that carry alpha virus expression cassettes, such as but not restricted to the semliki forest virus [29–34] or venezuelan equine encephalitis (herein designated "VEE") virus [25–28], that are capable of self-amplification.

In yet another object of the current invention, methods are provided for the administration of recombinant dsRP to eukaryotic cells and tissues, and the use of recombinant dsRP to induce an immune response or to cause a biological affect in a target cell population.

In a still further object of the current invention, compositions and methods are described for the delivery of dsRP to mammalian cells and tissues using bacterial vectors, and the use of said bacterial vectors carrying recombinant dsRP to induce an immune response or to cause a biological affect in a target cell population.

In another embodiment, the present invention relates to live bacteria that carry a recombinant dsRP containing one or more eukaryotic translation expression cassettes encoding dsRNA encoding IRES sequences that are functionally linked to one or more passenger genes.

In yet another embodiment of this invention, recombinant dsRP compositions are provided that incorporate an alphavirus expression cassette into said dsRP, thereby harnessing the mRNA-amplifying properties of said alpha virus, resulting in the generation of dsRP that are capable of substantively amplifying the mRNA of a passenger RNA-encoded gene in eukaryotic cells.

These and other objects of the present invention, which will be apparent from the detailed description of the invention provided hereinafter, have been met in one embodiment by providing compositions and methods for introducing and expressing a gene into eukaryotic cells, comprising infecting said cells with a recombinant dsRP carrying a eukaryotic translation expression cassette comprised of dsRNA sequences encoding an IRES and the green fluorescent protein (herein designated "GFP"), wherein said dsRP carrying said eukaryotic translation expression cassette is capable of expressing GFP in eukaryotic cells.

In another embodiment, the present invention relates to live bacteria that carry a recombinant dsRP containing one or more eukaryotic translation expression cassettes encoding dsRNA encoding IRES sequences that are functionally linked to one or more passenger genes.

In yet another embodiment of this invention, recombinant dsRP compositions are provided that incorporate an alphavirus expression cassette into said dsRP, thereby harnessing the mRNA-amplifying properties of said alpha virus, resulting in the generation of dsRP that are capable of substantively amplifying the mRNA of a passenger RNA-encoded gene in eukaryotic cells.

DESCRIPTION OF THE DRAWINGS

FIG. 1 is a schematic drawing showing the replication of dsRP nucleocapsids in bacterial cytoplasm.

FIG. 2 is a schematic drawing illustrating cloning cDNA copies of the mRNA produced by dsRP.

FIG. 3 is a schematic drawing illustrating the construction of recombinant dsRP segments using cDNA clones.

FIG. 4 is a schematic drawing illustrating the generation of recombinant dsRP nucleocapsids.

Figure 5:
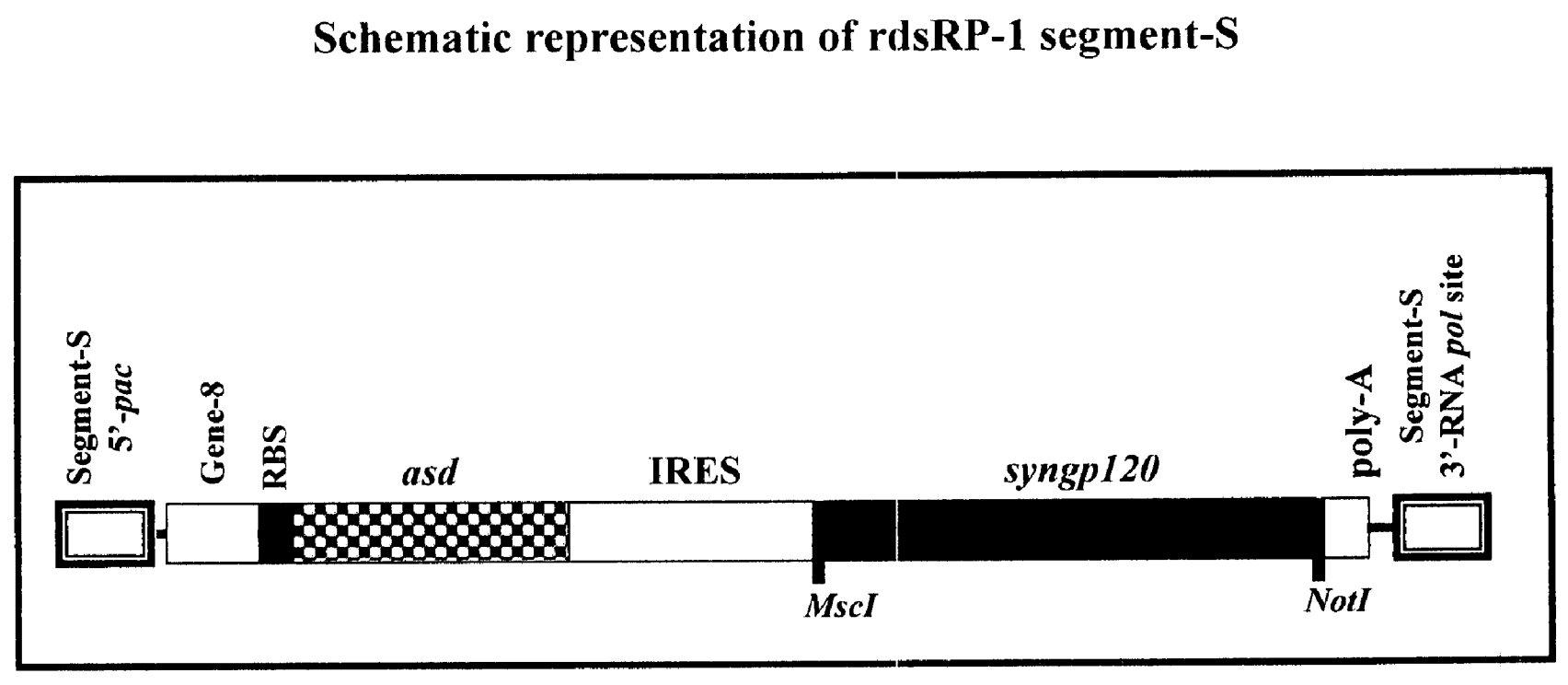

FIG. 5 is a schematic representation of rdsRP-1 segment-S.

FIG. 6 is a schematic representation of the recombinant segment-S in a self-amplifying rdsRP.

DETAILED DESCRIPTION OF THE INVENTION

As mentioned above in one embodiment of the present invention recombinant dsRP (herein referred to as "rdsRP") are provided that express dsRNA-encoded genes in eukaryote cells. Normally, dsRP-encoded genes are poorly translated in eukaryotic cells due to the lack of cap-independent eukaryotic translation signaling sequences that are necessary to launch efficient ribosome binding and the translation of mRNA sequences into protein. Below rdsRP are provided that produce mRNA molecules containing the appropriate translation initiation sequences that enable efficient recognition and translation in eukaryotic cells. It is surprising that only a simple modification to a prokaryotic virus (i.e. dsRP) results in efficient expression in a eukaryotic cell. This finding suggests that a partial evolutionary leap by a virus from prokaryote to eukaryote only requires the acquisition of small amounts of genetic information.

Recombinant DNA Techniques

The recombinant DNA procedures used in the construction of the following rdsRP, including PCR, restriction endonuclease (herein referred to as "RE") digestions, DNA ligation, agarose gel electrophoresis, DNA purification, and dideoxynucleotide sequencing, are described elsewhere [37–40](Miller, *A Short Course in Bacterial Genetics,* Cold Spring Harbor Laboratory Press, Cold Spring Harbor, N.Y. (1992); Bothwell et al, supra; and Ausubel et al, supra), bacteriophage-mediated transduction (de Boer, supra; Miller, supra; and Ausubel et al, supra), or chemical (Bothwell et al, supra; Ausubel et al, supra; Felgner et al, supra; and Farhood, supra), electroporation (Bothwel et al, supra; Ausubel et al, supra; and Sambrook, *Molecular Cloning: A Laboratory Manual,* Cold Spring Harbor Laboratory Press, Cold Spring Harbor, N.Y.) and physical transformation techniques (Johnston et al, supra; and Bothwell, supra). The genes can be incorporated on phage (de Boer et al, *Cell,* 56:641–649 (1989)), plasmids vectors (Curtiss et al, supra) or spliced into the chromosome (Hone et al, supra) of the target strain.

Gene sequences can be made synthetically using an Applied Biosystems ABI™ 3900 High-Throughput DNA Synthesizer (Foster City, Calif. 94404 U.S.A.) and procedures provided by the manufacturer. To synthesize large sequences i.e greater than 200 bp, a series of segments of the full-length sequence are generated by PCR and ligated together to form the full-length sequence using procedures well know in the art [41–43]. However, smaller sequences, i.e. those smaller than 200 bp, can be made synthetically in a single round using an Applied Biosystems ABI™ 3900

High-Throughput DNA Synthesizer (Foster City, Calif. 94404 U.S.A.) and procedures provided by the manufacturer.

Recombinant plasmids are introduced into bacterial strains by electroporation using a BioRad Gene-Pulser® set at 200Ω, 25 μF and 2.5 kV (BioRad Laboratories, Hercules, Calif.) [38]. Nucleotide sequencing to verify cDNA sequences is accomplished by standard automated sequencing techniques (Applied Biosystems automated sequencer, model 373A). DNA primers for DNA sequencing and polymerase chain reaction (herein referred to as "PCR") are synthesized using an Applied Biosystems ABI™ 3900 High-Throughput DNA Synthesizer (Foster City, Calif. 94404 U.S.A.).

Source of IRES Sequences mRNA molecules lacking a 5' cap modifier, which is normally added in the nucleus to nuclear mRNA transcripts and enhances ribosome recognition, are poorly translated in eukaryotic cells unless an IRES sequence is present upstream of the gene of interest. The particular IRES employed in the present invention is not critical and can be selected from any of the commercially available vectors that contain IRES sequences. Thus, IRES sequences are widely available and can be obtained commercially from plasmid pIRES2-EGFP (Clontech; [44]) by PCR using primers specific for the 5' and 3' ends of the IRES located at nucleotides 665–1251 in pIRES2-EGFP. The sequences in plasmid pIRES-EGFP can be obtained from the manufacturer clontech.com/techinfo/vectors/vectorsF-I/pdf/pIRES2-EGFPseq.pdf). A similar IRES can also be obtained from plasmid pCITE4a (Novagen, Madison Wis.; see also U.S. Pat. No. 4,937,190 which is herein incorporated by reference) by PCR using primers specific for the 5' and 3' ends of the CITE from nucleotides 16 to 518 in plasmid pCITE4a (the complete sequence of pCITE4a is available at novagen.com/docs/NDIS/69913-000.HTM). on plasmids pCITE4a-c (Novagen, URL:-novagen.com; U.S. Pat. No. 4,937,190 which is herein incorporated by reference); pSLIRES11 (Accession: AF171227; pPV (Accession # Y07702); pSVIRES-N (Accession #: AJ000156); Creancier et al. J. Cell Biol., 10: 275–281 (2000); Ramos and Martinez-Sala, RNA, 10: 1374–1383 (1999); Morgan et al. Nucleic Acids Res., 20: 1293–1299 (1992); Tsukiyama-Kohara et al. J. Virol., 66: 1476–1483 (1992); Jang and Wimmer et al. Genes Dev., 4: 1560–1572 (1990)), or on the dicistronic retroviral vector (Accession #: D88622); or found in eukaryotic cells such as the fibroblast growth factor 2 IRES for stringent tissue-specific regulation (Creancier, et al., J. Cell. Biol., 150:275 (2000)) or the Internal-ribosome-entry-site of the 3'-untranslated region of the mRNA for the beta subunit of mitochondrial $H^+$-ATP synthase (Izquierdo and Cuezva, Biochem. J., 346:849 (2000)).

Non-commercial sources of IRES's are also available and can be located as follows. Thus, plasmid pIRES-G (Hobbs, S. M. CRC Centre for Cancer Therapeutics, Institute of Cancer Research, Block F, 15, Cotswold Road, Belmont, Sutton, Surrey SM2 5NG, UK) will serve as source of IRES and the sequence of this plasmid is available (Genebank accession no. Y11034). Furthermore, an Internet search using the NCBI nucleotide database ncbi.nlm.nih.gov/entrez/query.fcgi?CMD=Display&DB=nucleotide) and the search parameter "IRES not patent" yields 41 Files containing IRES sequences. Finally, IRES cDNA can be made synthetically using an Applied Biosystems ABI™ 3900 High-Throughput DNA Synthesizer (Foster City, Calif. 94404 U.S.A.), using procedures provided by the manufacturer. To synthesize large IRES sequences such as the 502 bp IRES in pCITE4a, a series of segments are generated by PCR and ligated together to form the full-length sequence using procedures well know in the art [41–43]. Smaller IRES sequences such as the 53 bp IRES in hepatitis C virus (Genebank accession no. 1KH6_A; [45,46]) can be made synthetically in a single round using an Applied Biosystems ABI™ 3900 High-Throughput DNA Synthesizer (Foster City, Calif. 94404 U.S.A.) and procedures provided by the manufacturer.

Examples of Genes of Interest that Can Be Inserted in dsRP

In the present invention, the gene of interest (GOI) introduced on a eukaryotic translation expression cassette into the rdsRP may encode an immunogen, which may be either a foreign immunogen from viral, bacterial and parasitic pathogens, or an endogenous immunogen, such as but not limited to an autoimmune antigen or a tumor antigen. The immunogens may be the full-length native protein, chimeric fusions between the foreign immunogen and an endogenous protein or mimetic, a fragment or fragments thereof of an immunogen that originates from viral, bacterial and parasitic pathogens.

As used herein, "foreign immunogen" means a protein or fragment thereof, which is not normally expressed in the recipient animal cell or tissue, such as, but not limited to, viral proteins, bacterial proteins, parasite proteins, cytokines, chemokines, immunoregulatory agents, or therapeutic agents.

An "endogenous immunogen" means a protein or part thereof that is naturally present in the recipient animal cell or tissue, such as, but not limited to, an endogenous cellular protein, an immunoregulatory agent, or a therapeutic agent.

Alternatively or additionally, the immunogen may be encoded by a synthetic gene and may be constructed using conventional recombinant DNA methods (See above).

The foreign immunogen can be any molecule that is expressed by any viral, bacterial, or parasitic pathogen prior to or during entry into, colonization of, or replication in their animal host; the rdsRP may express immunogens or parts thereof that originate from viral, bacterial and parasitic pathogens. These pathogens can be infectious in humans, domestic animals or wild animal hosts.

The viral pathogens, from which the viral antigens are derived, include, but are not limited to, Orthomyxoviruses, such as influenza virus (Taxonomy ID: 59771; Retroviruses, such as RSV, HTLV-1 (Taxonomy ID: 39015), and HTLV-II (Taxonomy ID: 11909), Herpesviruses such as EBV Taxonomy ID: 10295); CMV (Taxonomy ID: 10358) or herpes simplex virus (ATCC #: VR-1487); Lentiviruses, such as HIV-1 (Taxonomy ID: 12721) and HIV-2 Taxonomy ID: 11709); Rhabdoviruses, such as rabies; Picomoviruses, such as Poliovirus (Taxonomy ID: 12080); Poxviruses, such as vaccinia (Taxonomy ID: 10245); Rotavirus (Taxonomy ID: 10912); and Parvoviruses, such as adeno-associated virus 1 (Taxonomy ID: 85106).

Examples of viral antigens can be found in the group including but not limited to the human immunodeficiency virus antigens Nef (National Institute of Allergy and Infectious Disease HIV Repository Cat. # 183; Genbank accession # AF238278), Gag, Env (National Institute of Allergy and Infectious Disease HIV Repository Cat. # 2433; Genbank accession # U39362), Tat (National Institute of Allergy and Infectious Disease HIV Repository Cat. # 827; Genbank accession # M13137), mutant derivatives of Tat, such as Tat-Δ31-45 (Agwale et al. *Proc. Natl. Acad. Sci.* In press. July 8th (2002)), Rev (National Institute of Allergy and Infectious Disease HIV Repository Cat. # 2088; Genbank accession # L14572), and Pol (National Institute of Allergy and Infectious Disease HIV Repository Cat. # 238; Genbank accession # AJ237568) and T and B cell epitopes of gp120 (Hanke and McMichael, AIDS Immunol Lett., 66:177 (1999); Hanke, et al., *Vaccine*, 17:589 (1999); Palker et al, *J. Immunol.*, 142:3612–3619 (1989)) chimeric derivatives of HIV-1 Env and gp120, such as but not restricted to fusion between gp120 and CD4 (Fouts et al., *J. Virol.* 2000, 74:11427–11436 (2000)); truncated or modified derivatives of HIV-1 env, such as but not restricted to gp140 (Stamatos et al. *J Virol*, 72:9656–9667 (1998)) or derivatives of HIV-1 Env and/or gp140 thereof (Binley, et al. *J Virol*, 76:2606–2616 (2002); Sanders, et al. *J Virol*, 74:5091–5100 (2000); Binley, et al. *J Virol*, 74:627–643 (2000)), the hepatitis B surface antigen (Genbank accession # AF043578; Wu et al, *Proc. Natl. Acad. Sci., USA*, 86:4726–4730 (1989)); rotavirus antigens, such as VP4 (Genbank accession # AJ293721; Mackow et al, *Proc. Natl. Acad. Sci., USA*, 87:518–522 (1990)) and VP7 (GenBank accession # AY003871; Green et al, *J. Virol.*, 62:1819–1823 (1988)), influenza virus antigens such as hemagglutinin or (GenBank accession # AJ404627; Pertmer and Robinson, Virology, 257:406 (1999)); nucleoprotein (GenBank accession # AJ289872; Lin et al, Proc. Natl. Acad. Sci., 97: 9654–9658 (2000))) herpes simplex virus antigens such as thymidine kinase (Genbank accession # AB047378; Whitley et al, *In: New Generation Vaccines*, pages 825–854).

The bacterial pathogens, from which the bacterial antigens are derived, include but are not limited to, *Mycobacterium spp.* (tubercolis antigens which may be used in the practice of the present invention are described in U.S. Pat. Nos. 5,955,077; 6,224,881; 6,384,018; 6,531,138; 6,596,218; U.S. published application 2002/0176867; and U.S. published application 2003/0143243 each of which are herein incorporated by reference), *Helicobacter pylori*, *Salmonella* spp., *Shigella* spp., *E. coli*, *Rickettsia* spp., *Listeria* spp., *Legionella pneumoniae*, *Pseudomonas* spp., *Vibrio* spp., and *Borellia burgdorferi*.

Examples of protective antigens of bacterial pathogens include the somatic antigens of enterotoxigenic *E. coli*, such as the CFA/I fimbrial antigen (Yamamoto et al., *Infect. Immun.*, 50:925–928 (1985)) and the nontoxic B-subunit of the heat-labile toxin (Klipstein et al., *Infect. Immun.*, 40:888–893 (1983)); pertactin of *Bordetella pertussis* (Roberts et al, *Vacc.*, 10:43–48 (1992)), adenylate cyclase-hemolysin of *B. pertussis* (Guiso et al, *Micro. Path.*, 11:423–431 (1991)), fragment C of tetanus toxin of *Clostridium tetani* (Fairweather et al., *Infect. Immun.*, 58:1323–1326 (1990)), OspA of *Borellia burgdorferi* (Sikand, et al. *Pediatrics*, 108:123–128 (2001); Wallich, et al. *Infect Immun*, 69:2130–2136 (2001)), protective paracrystalline-surface-layer proteins of *Rickettsia prowazekii* and *Rickettsia typhi* (Carl, et al. *Proc Natl Acad Sci USA*, 87:8237–8241 (1990)), the listeriolysin (also known as "Llo" and "Hly") and/or the superoxide dismutase (also know as "SOD" and "p60") of *Listeria monocytogenes* (Hess, J., et al. *Infect. Immun.* 65:1286–92 (1997); Hess, J., et al. *Proc. Natl. Acad. Sci.* 93:1458–1463 (1996); Bouwer, et al. *J. Exp. Med.* 175: 1467–71 (1992)), the urease of *Helicobacter pylori* (Gomez-Duarte, et al. *Vaccine* 16, 460–71 (1998); Corthesy-Theulaz, et al. *Infection & Immunity* 66, 581–6 (1998)), and the receptor-binding domain of lethal toxin and/or the protective antigen of *Bacillus anthrax* (Price, et al. *Infect. Immun.* 69, 4509–4515 (2001)).

The parasitic pathogens, from which the parasitic antigens are derived, include but are not limited to, *Plasmodium* spp., such as *Plasmodium falciparum* (ATCC#: 30145); *Trypanosome* spp., such as *Trypanosoma cruzi* (ATCC#: 50797); *Giardia* spp., such as *Giardia intestinalis* (ATCC#: 30888D); *Boophilus* spp., *Babesia* spp., such as *Babesia microti* (ATCC#: 30221); *Entamoeba* spp., such as *Entamoeba histolytica* (ATCC#: 30015); *Eimeria* spp., such as *Eimeria maxima* (ATCC# 40357); *Leishmania* spp. (Taxonomy ID: 38568); *Schistosome* spp., *Brugia* spp., *Fascida* spp., *Dirofilaria* spp., *Wuchereria* spp., and *Onchocerea* spp.

Examples of protective antigens of parasitic pathogens include the circumsporozoite antigens of *Plasmodium* spp. (Sadoff et al, *Science*, 240:336–337 (1988)), such as the circumsporozoite antigen of *P. bergerii* or the circumsporozoite antigen of *P. falciparum*; the merozoite surface antigen of *Plasmodium* spp. (Spetzler et al, *Int. J. Pept. Prot. Res.*, 43:351–358 (1994)); the galactose specific lectin of *Entamoeba histolytica* (Mann et al, *Proc. Natl. Acad. Sci., USA*, 88:3248–3252 (1991)), gp63 of *Leishmania* spp. (Russell et al, *J. Immunol.*, 140:1274–1278 (1988); Xu and Liew, Immunol., 84: 173–176 (1995)), gp46 of Leishmania major (Handman et al, Vaccine, 18: 3011–3017 (2000) paramyosin of *Brugia malayi* (Li et al, *Mol. Biochem. Parasitol.*, 49:315–323 (1991)), the triose-phosphate isomerase of *Schistosoma mansoni* (Shoemaker et al, *Proc. Natl. Acad. Sci., USA*, 89:1842–1846 (1992)); the secreted globin-like protein of *Trichostrongylus colubriformis* (Frenkel et al, *Mol. Biochem. Parasitol.*, 50:27–36 (1992)); the glutathione-S-transferase's of *Frasciola hepatica* (Hillyer et al, *Exp. Parasitol.*, 75:176–186 (1992)), *Schistosoma bovis* and *S. japonicum* (Bashir et al, *Trop. Geog. Med.*, 46:255–258 (1994)); and KLH of *Schistosoma bovis* and *S. japonicum* (Bashir et al, supra).

As mentioned earlier, the dsRP vaccine may encode an endogenous immunogen, which may be any cellular protein, immunoregulatory agent, or therapeutic agent, or parts thereof, that may be expressed in the recipient cell, including but not limited to tumor, transplantation, and autoimmune immunogens, or fragments and derivatives of tumor, transplantation, and autoimmune immunogens thereof. Thus, in the present invention, dsRP may encode tumor, transplant, or autoimmune immunogens, or parts or derivatives thereof. Alternatively, the dsRP may encode synthetic genes (made as described above), which encode tumor-specific, transplant, or autoimmune antigens or parts thereof.

Examples of tumor specific antigens include prostate specific antigen (Gattuso et al, *Human Pathol.*, 26:123–126 (1995)), TAG-72 and CEA (Guadagni et al, *Int. J. Biol. Markers*, 9:53–60 (1994)), MAGE-1 and tyrosinase (Coulie et al, *J. Immunothera.*, 14:104–109 (1993)). Recently it has been shown in mice that immunization with non-malignant cells expressing a tumor antigen provides a vaccine effect, and also helps the animal mount an immune response to clear malignant tumor cells displaying the same antigen (Koeppen et al, *Anal. N.Y. Acad. Sci.*, 690:244–255 (1993)).

Examples of transplant antigens include the CD3 molecule on T cells (Alegre et al, *Digest. Dis. Sci.*, 40:58–64 (1995)). Treatment with an antibody to CD3 receptor has been shown to rapidly clear circulating T cells and reverse cell-mediated transplant rejection (Alegre et al, supra).

Examples of autoimmune antigens include IAS β chain (Topham et al, *Proc. Natl. Acad. Sci., USA*, 91:8005–8009 (1994)). Vaccination of mice with an 18 amino acid peptide from IAS β chain has been demonstrated to provide protection and treatment to mice with experimental autoimmune encephalomyelitis (Topham et al, supra).

Introduction of Sequences into dsRP

Figure 2:
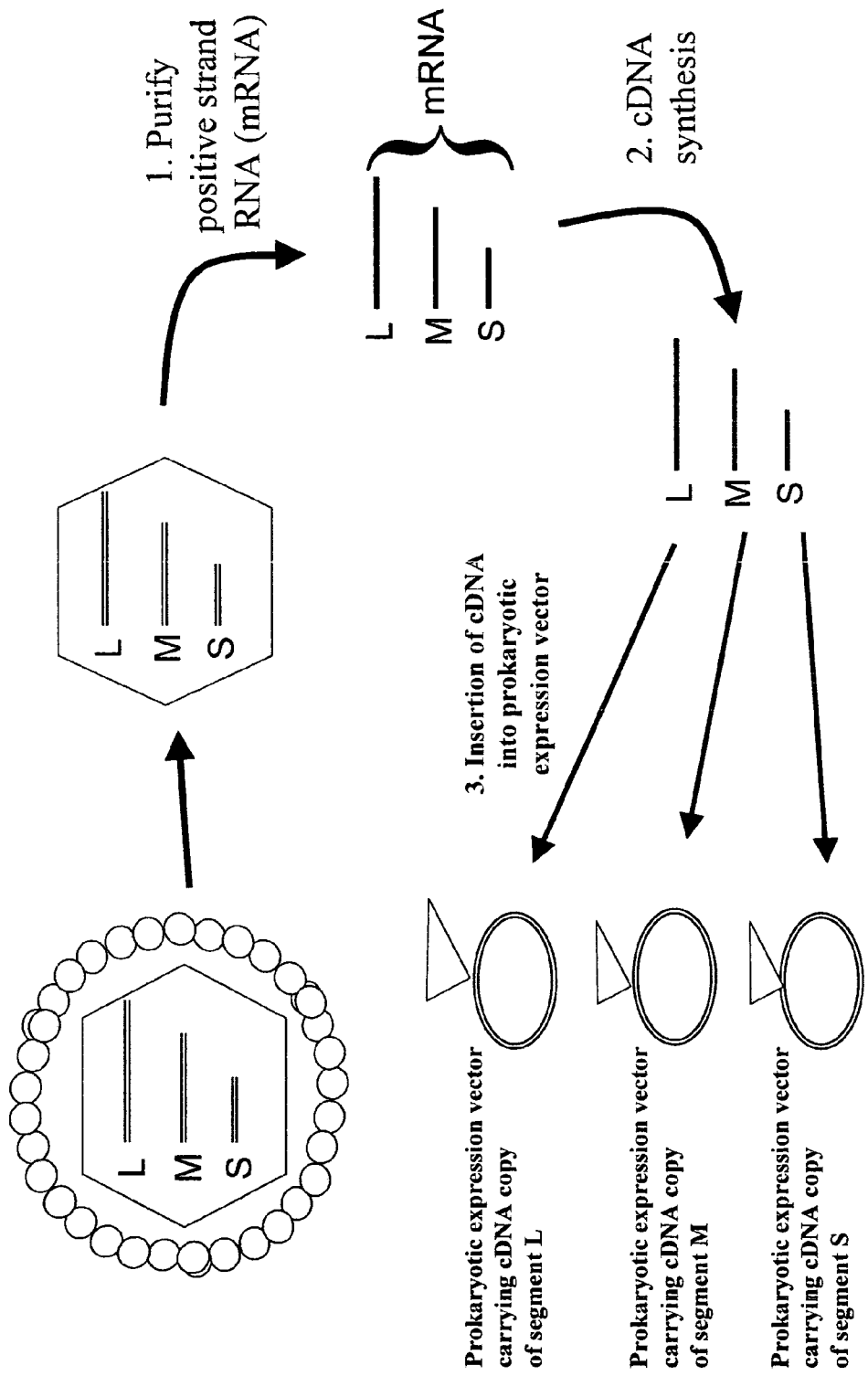
Figure 3:
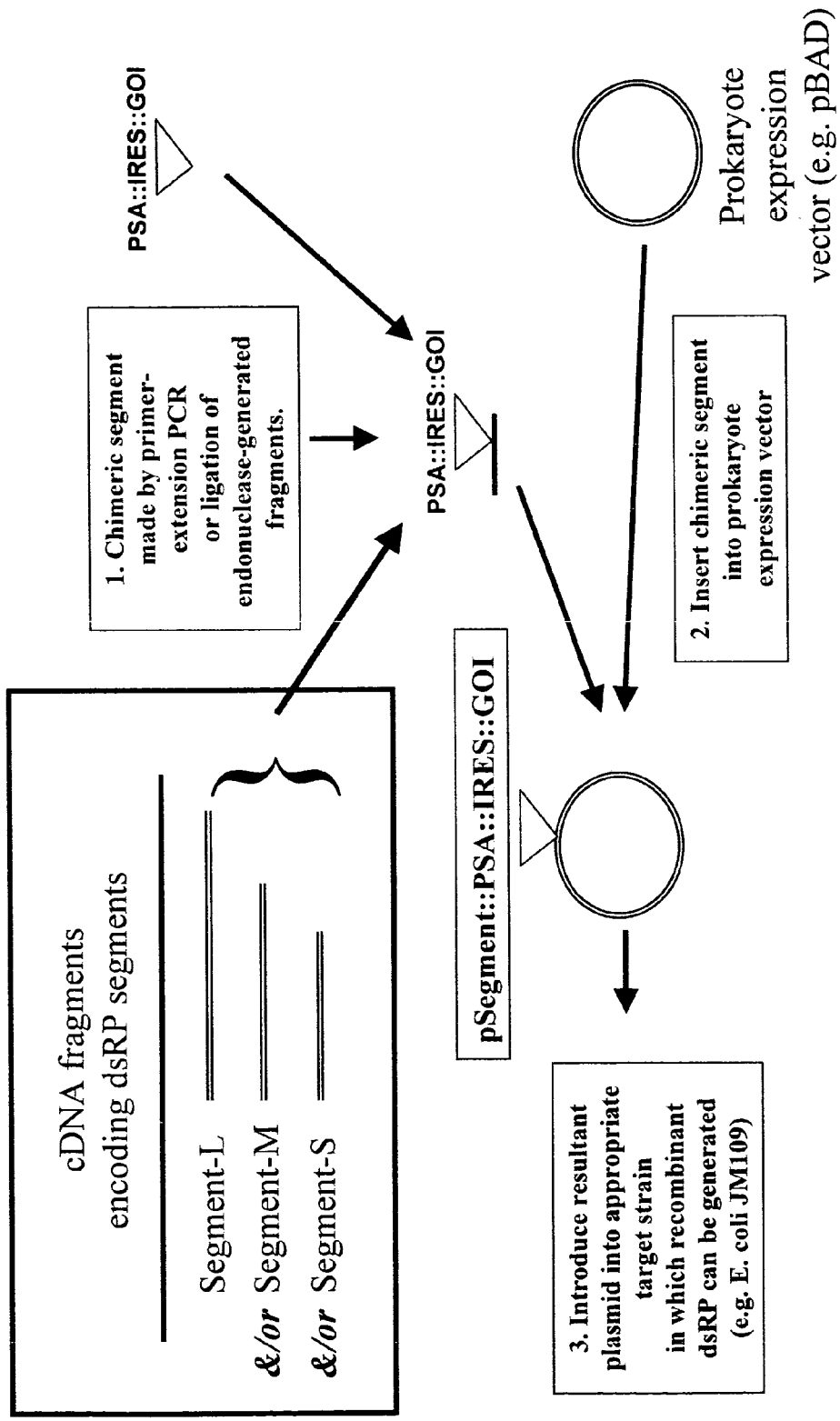
Figure 4:
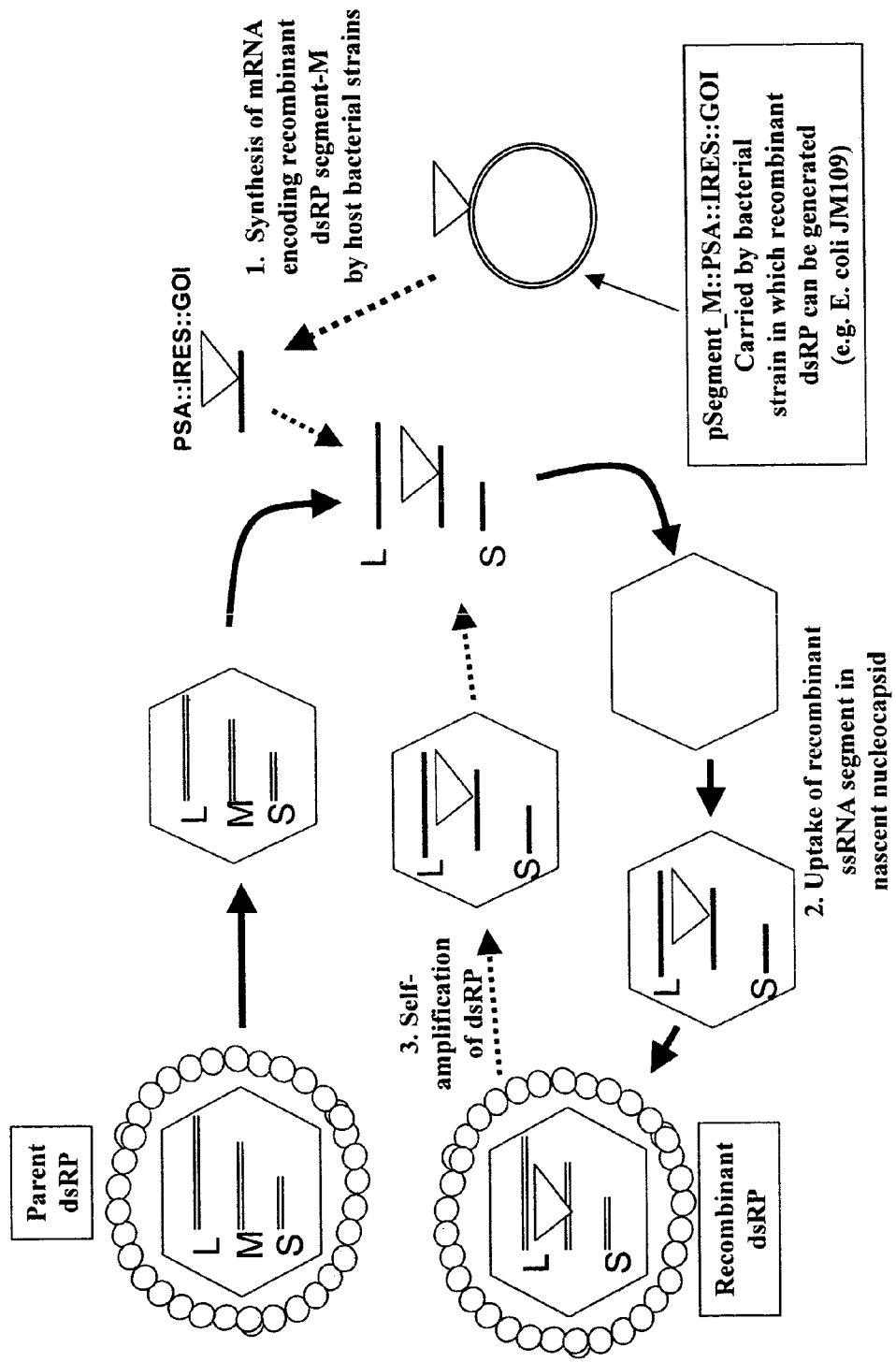

To manipulate dsRP, cDNA copies of the mRNA segments L, M and S are generated and inserted into a prokaryotic expression vector (FIG. 2) using procedures well know in the art (Ausubel et al, supra; and Sambrook, supra). These cloned cDNA copies of the mRNA are used as target sequences into which the sequence of interest that encodes the GOI is inserted (FIGS. 3 and 4).

To generate rdsRP that retain the capacity to produce infectious phage, the sequence that is being incorporated into the dsRP can be inserted into an unessential region of a dsRP, such as but not limited to the Pst I restriction endonuclease site in the cDNA clone of M segment [17]. Alternatively, standard PCR techniques can be used to introduce RE digestion sites in a non-essential region, such as between the pac sequence in segment-M and gene-10 in Phi-6 [17].

Alternatively, the sequence that is being incorporated into the dsRP can replace genes of the dsRP that are not required for the production of stable nucleocapsids, such as but not limited to the replacement of gene-10 in segment-M, gene-3 in segment-M, gene-9 in segment-S, gene-12 in segment-S; alternatively the sequence being inserted into the dsRP. Thus, plasmid pLM656 (From Dr. L Mindich, Department of Microbiology, The Public Health Research Institute NY, N.Y.; [17]), carries the complete cDNA copy of segment-M, is digested with RE Pst I and the resultant linear plasmid DNA is treated with T4 DNA polymerase to remove the single stranded sequences created by Pst I thereby creating blunt-ends. Sequences of interest can be inserted into Pst I-digested, T4 polymerase-treated pLM656 DNA by standard blunt-end ligation techniques using T4 DNA ligase (Ausubel et al, supra; and Sambrook, supra). The resultant plasmid carries a cDNA copy of the recombinant segment M produce mRNA's that carry the sequence of interest.

Introduction of Functional Eukaryotic Translation Expression Cassettes into dsRP As indicated above, in one embodiment of the current invention, sequences of interest can encode a functional eukaryotic translation expression cassette. A simple approach to obtain a functional eukaryotic translation expression cassette is to introduce an IRES functionally linked to a gene of interest (herein referred to as GOI), which is normally placed downstream (i.e. 3') of the IRES.

Sequences encoding the IRES can be amplified by PCR using primers specific for the 5' and 3' ends of the IRES sequence; the GOI can be amplified using primers specific for the 5' and 3' ends of the transcribed region of the GOI or parts thereof. RE digestion sites (e.g. Not I, Eco RI, Sal I) can be introduced into the primers so that the resultant PCR-generated products can be digested with said REs and fused to a positive-selection allele (herein referred to as "PSA"), which can be amplified using PCR primers that place RE recognition sites (e.g. Not I) at the 5' and 3' ends of the PSA. The particular PSA used in the current invention is not critical thereto and can be the $kan^r$ allele in plasmid pUC18K1 [47]; the *Escherichia coli* asd allele in plasmid pYA292 (Galan, et al., *Gene* 94:29–35 (1990); Genbank accession no. V00262).

The resultant chimeric fragment encoding PSA::IRES::GOI is inserted into an RE-digested plasmid containing the target dsRP segment (e.g. insertion into the M-segment using Pst I-digested, T4 polymerase-treated pLM656 DNA and blunt-end ligation to the PSA::IRES::GOI sequence, as above (Ausubel et al, supra; and Sambrook, supra). The resultant plasmid, carries a cDNA copy of the recombinant segment and produces mRNA's that bear a PSA for maintenance of the recombinant segment in the rdsRP, a cap-independent translation recognition sequence (i.e. IRES) and an GOI reporter gene.

Generation of rdsRP

An application of the current invention entails the use of enriched or purified rdsRP for direct administration to eukaryotic cells or tissues. The particular dsRP is not critical to the present invention and includes but is not restricted to one of Phi-6 (Genbank accession no. M17461 (Segment-L), M17462 (Segment-M), M12921 (Segment-S)); Phi-8 (Genbank accession no. AF226851 (Segment-L), NC_003300 (Segment-M), AF226853 (Segment-S)); and Phi-13 (Genbank accession no. AF261668 (Segment-L), AF261668 (Segment-M), NC_003714 (Segment-S)) and are available from Dr. L. Mindich at Department of Microbiology, Public Health Research Institute, NY, N.Y.

DsRP phi-6 normally replicates in *Pseudomonas syringae* [5]; dsRP phi-8, phi-11, phi-12 and phi-13 replicate in *Escherichia coli* strain JM109 (American type tissue culture collection (herein "ATCC") # 53323) and O-antigen negative mutants of *Salmonella enterica* serovar *Typhimurium* (herein designated "*S. typhimurium*") [5,14–16].

Alternatively, the cDNA sequences encoding the dsRP can be generated synthetically using an Applied Biosystems ABI™ 3900 High-Throughput DNA Synthesizer (Foster City, Calif. 94404 U.S.A.) and procedures provided by the manufacturer. To synthesize the cDNA copies of segments L, M and S a series of segments of the full-length sequence are generated by PCR and ligated together to form the full-length segment using procedures well know in the art [41–43]. Briefly, synthetic oligonucleotides 100–200 nucleotides in length (i.e. preferably with sequences at the 5'- and 3' ends that match at the 5' and 3' ends of the oligonucleotides that encodes the adjacent sequence) are produced using an automated DNA synthesizer (E.g. Applied Biosystems ABI™ 3900 High-Throughput DNA Synthesizer (Foster City, Calif. 94404 U.S.A.)). Using the same approach, the complement oligonucleotides are synthesized and annealed with the complementary partners to form double stranded oligonucleotides. Pairs of double stranded oligonucleotides (i.e. those that encode adjacent sequences) and joined by ligation to form a larger fragment. These larger fragments are purified by agarose gel electrophoresis and isolated using a gel purification kit (E.g. The QIAEX® II Gel Extraction System, from Qiagen, Santa Cruz, Calif., Cat. No. 12385). This procedure is repeated until the full-length DNA molecule is created. After each round of ligation the fragments can be amplified by PCR to increase the yield. Procedures for de novo synthetic gene construction are well known in the art, and are described elsewhere (Andre et al., supra, (1998); et al., Haas supra, (1996)); alternatively synthetic genes can be purchased commercially, e.g. from the Midland Certified Reagent Co. (Midland, Tex.).

To genetically manipulate dsRP, phage are amplified in a bacterial host strain, including but not limited to *Pseudomonas syringae* [5], *Escherichia coli* strain JM109 (American type tissue culture collection (herein "ATCC") # 53323) and O-antigen negative mutants of *Salmonella enterica* serovar *Typhimurium* (herein designated "*S. typhimurium*") [5,14–16]. and purified to the level commensurate to the desired in vitro or in vivo application. RdsRP are produced from strains carrying the plasmids that encode the cDNA copies of the manipulated segments (i.e. the segments containing the inserted sequences of interest encoding the functional eukaryotic translation expression cassette, catalytic RNA or antisense RNA).

To produce rdsRP in *Escherichia coli* (e.g. strain JM109), the cDNA-containing plasmids (e.g. pLM656-PSA::IRES::EGFP) are introduced into target bacterial strains by standard bacterial transformation methods (Ausubel et al, supra; and Sambrook, supra) and antibiotic-resistant transformants are isolated in solid media (e.g. Luria-Bertani agar (herein referred to as LBA), Difco Detroit Mich.) containing the appropriate antibiotic (Antibiotics for inclusion in bacteriological media are available from Sigma, St. Louis Mo.) at a concentration that is equal to, or greater than, the minimal inhibitory concentration (also referred to as the "mic").

The bacterial isolates are cultured at temperatures that range from 25° C. to 44° C. for 16 to 48 hr; however, it is preferable to culture the transformants at 37° C. for 16 hr. Colonies that grow on the selective solid media are subsequently isolated and purified by standard methods (Ausubel et al, supra; and Sambrook, supra). To verify that the antibiotic-resistant isolates carrying the plasmid of interest, individual isolates are cultured in liquid media (e.g. Luria-Bertani broth (herein referred to as "LB"), Difco Mo.). The transformants are harvested after cultures reach an optical density at 600 nm ($OD_{600}$) of 0.001 to 4.0, preferably 0.9, relative to the $OD_{600}$ a sterile LB control. Plasmid DNA is isolated from these cultures and analysed by RE digestion using enzymes that generate a defined digestion pattern based on the predicted sequence of the recombinant plasmid, including but not limited to Eco RI, Pst I, Hind III, Hae I, Sau IIIa, Not I, and Sal I. Alternatively or in addition, the plasmids can be screened by PCR using primers that amplify defined fragments within the recombinant plasmid, including but not limited to PCR primers that amplify the dsRP segment, the PSA, the IRES and the GOI. The PCR primers for the amplifications are designed using Clone Manager® software version 4.1 (Scientific and Educational Software Inc., Durhan N.C.). This software enables the design PCR primers and identifies RE sites that are compatible with the specific DNA fragments being manipulated. PCRs are conducted in a Strategene Robocycler, model 400880 (Strategene) and primer annealing, elongation and denaturation times in the PCRs are set according to standard procedures (Ausubel et al, supra). The RE digestions and the PCRs are subsequently analyzed by agarose gel electrophoresis using standard procedures (Ausubel et al, supra; and Sambrook, supra). A positive clone is defined as one that displays the appropriate RE pattern and/or PCR pattern. Plasmids identified through this procedure can be further evaluated using standard DNA sequencing procedures, as described above.

Having identified the desired transformants, individual strains are stored in a storage media, which is LB containing 50% (v/v) glycerol; Bacterial isolates are harvested from solid media using a sterile cotton wool swab and suspended in storage media at a density of $10^9$ cfu/ml and the suspensions are stored at −80° C.

Isolation and Purification of rdsRP

Batches of rdsRP are generated by replicating a parent rdsRP in the bacterial transformant said expresses the recombinant segment (FIG. 4). Methods for incorporation of recombinant segments into dsRP and for the subsequent replication, isolation and purification of the resultant rdsRP are well known in the art and have been published extensively in detail elsewhere (Mindich, et al. *J Virol* 66, 2605–10 (1992); Mindich, et al. *Virology* 212:213–217 (1995); Mindich, et al., *J Bacteriol* 181:4505–4508 (1999); Qiao, et al., *Virology* 275:218–224 (2000); Qiao, et al., *Virology* 227:103–110 (1997); Olkkonen, et al., *Proc Natl Acad Sci USA* 87:9173–9177 (1990); Onodera, et al., *J Virol* 66, 190–196 (1992)).

Development of rdsRP that Express an Adjuvant

Recombinant dsRP can be constructed that encode an immunogen and an adjuvant, and can be used to increase host responses to the dsRP. Alternatively, recombinant dsRP can be constructed that encode an adjuvant, in mixtures with other dsRP to increase host responses to immunogens encoded by the partner rdsRP.

The particular adjuvant encoded by the rdsRP is not critical to the present invention and may be the A subunit of cholera toxin (i.e. CtxA; GenBank accession no. X00171, AF175708, D30053, D30052), or parts thereof (E.g. the A1 domain of the A subunit of Ctx (i.e. CtxA1; GenBank accession no. K02679)), from any classical *Vibrio cholerae* (E.g. *V. cholerae* strain 395, ATCC # 39541) or El Tor *V. cholerae* (E.g. *V. cholerae* strain 2125, ATCC # 39050) strain. Alternatively, any bacterial toxin that increases cellular cAMP levels, such as a member of the family of bacterial adenosine diphosphate-ribosylating exotoxins (Krueger and Barbier, Clin. Microbiol. Rev., 8:34 (1995)), may be used in place of CtxA, for example the A subunit of heat-labile toxin (referred to herein as EltA) of enterotoxigenic *Escherichia coli* (GenBank accession # M35581), pertussis toxin S1 subunit (E.g. ptxS1, GenBank accession # AJ007364, AJ007363, AJ006159, AJ006157, etc.); as a further alternative the adjuvant may be one of the adenylate cyclase-hemolysins of *Bordetella pertussis* (ATCC # 8467), *Bordetella bronchiseptica* (ATCC # 7773) or *Bordetella parapertussis* (ATCC # 15237), E.g. the cyaA genes of *B. pertussis* (GenBank accession no. X14199), *B. parapertussis* (GenBank accession no. AJ249835) or *B. bronchiseptica* (GenBank accession no. Z37112).

Alternatively, the particular the adjuvant may be devoid of ADP-ribosyltransferase activity and may be any derivative of the A subunit of cholera toxin (i.e. CtxA; GenBank accession no. X00171, AF175708, D30053, D30052,), or parts thereof (i.e. the A1 domain of the A subunit of Ctx (i.e. CtxA1; GenBank accession no. K02679)), from any classical *Vibrio cholerae* (E.g. *V. cholerae* strain 395, ATCC # 39541) or El Tor *V. cholerae* (E.g. *V. cholerae* strain 2125, ATCC # 39050) that lack ADP-ribosyltransferase catalytic activity but retain the structural integrity, including but not restricted to replacement of arginine-7 with lysine (herein referred to as "R7K"), serine-61 with lysine (S61K), serine-63 with lysine (S63K), valine-53 with aspartic acid (V53D), valine-97 with lysine (V97K) or tyrosine- 104 with lysine (Y104K), or combinations thereof. Alternatively, the particular ADP-ribosyltransferase toxin that is devoid of ADP-ribosyltransferase activity may be any derivative of cholera toxin that fully assemble, but are nontoxic proteins due to mutations in the catalytic-site, or adjacent to the catalytic site, respectively. Such mutants are made by conventional site-directed mutagenesis procedures, as described above.

As a further alternative, the adjuvant of ADP-ribosyltransferase activity may be any derivative of the A subunit of heat-labile toxin (referred to herein as "LTA" of enterotoxigenic *Escherichia coli* (GenBank accession # M35581) isolated from any enterotoxigenic *Escherichia coli*, including but not restricted to *E. coli* strain H10407 (ATCC # 35401) that lack ADP-ribosyltransferase catalytic activity but retain the structural integrity, including but not restricted to R7K, S61K, S63K, V53D, V97K or Y104K, or combinations thereof. Alternatively, the particular ADP-ribosyltransferase toxin that is devoid of ADP-ribosyltransferase activity may be any derivative of cholera toxin that fully assemble, but are nontoxic proteins due to mutations in the catalytic-site, or adjacent to the catalytic site, respectively. Such mutants are made by conventional site-directed mutagenesis procedures, as described above.

Development of dsRP that Express an Immunoregulatory Agent

Recombinant dsRP can be constructed that encode an immunogen and a cytokine, and can be used to increase host responses to the dsRP. Alternatively, recombinant dsRP can be constructed that encode said cytokine alone, in mixtures with other dsRP to increase host responses to immunogens encoded by the partner rdsRP.

The particular cytokine encoded by the rdsRP is not critical to the present invention includes, but not limited to, interleukin-4 (herein referred to as "IL-4"; Genbank accession no. AF352783 (Murine IL-4) or NM_000589 (Human IL-4)), IL-5 (Genbank accession no. NM_010558 (Murine IL-5) or NM_000879 (Human IL-5)), IL-6 (Genbank accession no. M20572 (Murine IL-6) or M29150 (Human IL-6)), IL-10 (Genbank accession no. NM_010548 (Murine IL-10) or AF418271 (Human IL-10)), Il-$12_{p40}$ (Genbank accession no. NM_008352 (Murine IL-12 p40) or AY008847 (Human IL-12 p40)), IL-$12_{p70}$ (Genbank accession no. NM_008351/NM_008352 (Murine IL-12 p35/40) or AF093065/AY008847 (Human IL-12 p35/40)), TGFβ (Genbank accession no. NM_011577 (Murine TGFβ1) or M60316 (Human TGFβ1)), and TNFα Genbank accession no. X02611 (Murine TNFα) or M26331 (Human TNFα)).

Recombinant DNA and RNA procedures for the introduction of functional eukaryotic translation expression cassettes to generate rdsRP capable of expressing an immunoregulatory agent in eukaryotic cells or tissues are described above, wherein said immunoregulatory agent is the GOI.

Development of Self-amplifying dsRP

RdsRP can be constructed that carry an alpha-virus self-amplifying expression system (Pushko, et al., Virology 239:389–401 (1997); Caley, et al. J Virol 71:3031–3038 (1997); Mossman, et al., J Virol 70, 1953–1960 (1996); Zhou, et al., Vaccine 12:1510–1514 (1994)) and are used to significantly elevate the expression of the GOI. The particular alpha-virus self-amplifying expression system is not critical to the present invention and can be selected from semliki forest virus, such as but not limited to the semliki forest virus replicon in commercially available plasmid pSFV1 from Invitrogen Inc., or sequences encoding the nonstructural protein precursor and replicase recognition sequences of Venezuela equine encephalitis virus (i.e Genbank accession no. L04653).

Recombinant DNA, PCR, RE and sequence analysis procedures for the introduction of functional eukaryotic translation expression cassettes into rdsRP that incorporates an alpha-virus self-amplifying expression system capable functionally linked to an immunogen, immunoregulatory agent, or therapeutic agent, are described above, wherein said immunoregulatory agent constitutes part of the GOI and the immunogen, immunoregulatory agent or therapeutic agent are placed downstream of the replicase recognition sequence (Genbank accession no. L04653), as described (Pushko, et al., Virology 239:389–401 (1997); Caley, et al. J Virol 71:3031–3038 (1997); Mossman, et al., J Virol 70, 1953–1960 (1996); Zhou, et al., Vaccine 12:1510–1514 (1994)).

Administration of rdRP to Dendritic Cells In Vitro

The present invention can be used in vaccination regimens, wherein human derived dendritic cells are pulsed with the rdsRP and subsequently injected into an animal, intravenously, subcutaneously or intramuscularly. Such in vitro vaccination protocols are useful for the induction of anti-tumor immune responses.

Methods for the production and culture of dendritic cells are well known in the art and described elsewhere (Sallusto et al. 1994)). In short, human PBMCs are separated from the blood of healthy donors by centrifugation in Histopaque 1077 (Sigma, St. Louis, Mo.). The cells are enriched for monocytes (90–95% pure) using the StemSep Monocyte Enrichment Cocktail and a magnetic negative-selection column protocol (StemSep, Vancouver, British Columbia). Following enrichment, the monocytes are plated in RPMI 1640 (Gibco BRL: Grand Island, N.Y.) and incubated for 2 hours at 37° C. in a 5% $CO_2$ (37° C./5% $CO_2$). Non-adherent cells and media are removed and replaced with complete DC media, which comprises of RPMI 1640 supplemented with 10% fetal bovine serum (Gibco-BRL), 1% sodium pyruvate (Sigma), 1% non-essential amino acids (Gibco-BRL), Gentamycin (Gibco-BRL), 50 μM β-mecaptoethanal (Sigma), 10 μM Hepes (Sigma), 35 ng/ml interleukin-4 (IL-4, R+D Systems, Minnesota, Minn.), and 50 ng/ml granulocyte/monocyte-colony stimulating factor (GM-CSF, R+D Systems). Cells develop the appearance and cell surface phenotype of immature MDDCs after 4 days in culture at 37° C. 5% $CO_2$ environment, as confirmed by microscopy.

The DCs are analysed by flow cytometry at various times during the procedure to ensure that the appropriate antigen presenting properties are activated. The DCs are harvested in phosphate buffered saline (Gibco-BRL) supplemented with 2% human AB serum (Sigma) and 0.1% azide (Sigma), stained with R-phycoerythrin (PE)-anti-CD80, FITC-anti-CD83, PE-anti-CD86, PE-anti-CD25, PE-anti-HLA-ABC, and PE-anti-HLA-DR, (Becton Dickerson Pharmingen: San Deigo, Calif.) and fixed in 2% paraformaldehyde (Sigma) in PBS. Single-label flow cytometry data are collected using a FACSCaliber® (Beckmon Dickerson); expression of maturation markers in large cells is analyzed using CellQuest® (Beckmon Dickerson) and FlowJo® software (TreeStar, Stanford, Calif.).

To assess the cytokines produced by the DCs, Semi-quantitative ELISA assays for IL-6, TNF-α, IL-10, IL-12 p40, and IL-12 p70 (R+D Systems) were performed according to manufacturers instructions. In those experiments where cell surface data was not acquired, the cells and supernatants were frozen at −20° C. in the wells in which they were plated. The cells and supernatants were thawed and spun at 2000 RPM for 15 minutes to remove particulate matter immediately before ELISA assays were performed. In other experiments, the cell supernatants were reserved and either incorporated immediately into the ELISA protocol or frozen at −20° C.

Formulation of rdsRP Vaccines for In Vivo Administration

The specific method used to formulate the novel rdsRP vaccines described herein is not critical to the present invention and can be selected from a physiological buffer (Felgner et al., U.S. Pat. No. 5,589,466 (1996)); aluminum phosphate or aluminum hydroxyphosphate (e.g. Ulmer et al., Vaccine, 18:18 (2000)), monophosphoryl-lipid A (also referred to as MPL or MPLA; Schneerson et al. J. Immunol., 147: 2136–2140 (1991); e.g. Sasaki et al. Inf. Immunol., 65: 3520–3528 (1997); Lodmell et al. Vaccine, 18: 1059–1066 (2000)), QS-21 saponin (e.g. Sasaki, et al., J. Virol., 72:4931

(1998); dexamethasone (e.g. Malone, et al., J. Biol. Chem. 269:29903 (1994); CpG DNA sequences (Davis et al., J. Immunol., 15:870 (1998); or lipopolysaccharide (LPS) antagonist (Hone et al., supra (1997)).

Administration of rdsRP

The rdsRP vaccine can be administered directly into animal tissues by intravenous, intramuscular, intradermal, intraperitoneally, intranasal and oral inoculation routes. The specific method used to introduce the rdsRP vaccines described herein into the target animal tissue is not critical to the present invention and can be selected from previously described vaccination procedures (Wolff, et al., *Biotechniques* 11:474–85 (1991); Johnston and Tang, Methods Cell Biol 43:353–365 (1994); Yang and Sun, *Nat Med* 1:481–483 (1995); Qiu, et al., Gene Ther. 3:262–8 (1996); Larsen, et al., *J. Virol.* 72:1704–8 (1998); Shata and Hone *J. Virol.* 75:9665–9670 (2001); Shata, et al., *Vaccine* 20:623–629 (2001); Ogra, et al., *J Virol* 71:3031–3038 (1997); Buge, et al., *J. Virol.* 71:8531–8541 (1997);Belyakov, et al., *Nat. Med.* 7, 1320–1326 (2001); Lambert, et al., *Vaccine* 19:3033–3042 (2001); Kaneko, et al. *Virology* 267: 8–16 (2000); Belyakov, et al., *Proc Natl Acad Sci USA* 96:4512–4517 (1999).

Oral Administration of rdsRP with Bacterial Vaccine Vectors

Oral vaccination of the target animal with the rdsRP of the present invention can also be achieved using a non-pathogenic or attenuated bacterial vaccine vector. The amount of the bacterial vaccine vector to be administered with the rdsRP of the present invention will vary depending on the species of the subject, as well as the disease or condition that is being treated. Generally, the dosage employed will be about $10^3$ to $10^{11}$ viable organisms, preferably about $10^5$ to $10^9$ viable organisms.

The bacterial DNA vaccine vector and the rdsRP are generally administered along with a pharmaceutically acceptable carrier or diluent. The particular pharmaceutically acceptable carrier or diluent employed is not critical to the present invention. Examples of diluents include a phosphate buffered saline, buffer for buffering against gastric acid in the stomach, such as citrate buffer (pH 7.0) containing sucrose, bicarbonate buffer (pH 7.0) alone (Levine et al, *J. Clin. Invest.,* 79:888–902 (1987); and Black et al *J. Infect. Dis.,* 155:1260–1265 (1987)), or bicarbonate buffer (pH 7.0) containing ascorbic acid, lactose, and optionally aspartame (Levine et al, *Lancet, II:*467–470 (1988)). Examples of carriers include proteins, e.g., as found in skim milk, sugars, e.g., sucrose, or polyvinylpyrrolidone. Typically these carriers would be used at a concentration of about 0.1–90% (w/v) but preferably at a range of 1–10% (w/v).

EXAMPLE 1

Recombinant DNA Procedures

Restriction endonucleases (herein "Res"); New England Biolabs Beverly, Mass.), T4 DNA ligase (New England Biolabs, Beverly, Mass.) and Taq polymerase (Life technologies, Gaithersburg, Md.) were used according to the manufacturers' protocols; Plasmid DNA was prepared using small-scale (Qiagen Miniprep$^R$ kit, Santa Clarita, Calif.) or large-scale (Qiagen Maxiprep$^R$ kit, Santa Clarita, Calif.) plasmids DNA purification kits according to the manufacturer's protocols (Qiagen, Santa Clarita, Calif.); Nuclease-free, molecular biology grade milli-Q water, Tris-HCl (pH 7.5), EDTA pH 8.0, 1M $MgCl_2$, 100% (v/v) ethanol, ultra-pure agarose, and agarose gel electrophoresis buffer were purchased from Life technologies, Gaithersburg, Md. RE digestions, PCRs, DNA ligation reactions and agarose gel electrophoresis were conducted according to well-known procedures (Sambrook, et al., supra (1989); (Ausubel, et al., supra (1990)).

Nucleotide sequencing to verify the DNA sequence of each recombinant plasmid described in the following examples was accomplished by conventional automated DNA sequencing techniques using an Applied Biosystems automated sequencer, model 373A.

PCR primers were purchased from the University of Maryland Biopolymer Facility (Baltimore, Md.) and were synthesized using an Applied Biosystems DNA synthesizer (model 373A). PCR primers were used at a concentration of 200 μM and annealing temperatures for the PCR reactions were determined using Clone manager software version 4.1 (Scientific and Educational Software Inc., Durhan N.C.). PCRs were conducted in a Strategene Robocycler, model 400880 (Strategene, La Jolla, Calif.). The PCR primers for the amplifications are designed using Clone Manager® software version 4.1 (Scientific and Educational Software Inc., Durhan N.C.). This software enabled the design PCR primers and identifies RE sites that were compatible with the specific DNA fragments being manipulated. PCRs were conducted in a Strategene Robocycler, model 400880 (Strategene) and primer annealing, elongation and denaturation times in the PCRs were set according to standard procedures (Ausubel et al, supra). The RE digestions and the PCRs were subsequently analyzed by agarose gel electrophoresis using standard procedures (Ausubel et al, supra; and Sambrook, supra). A positive clone is defined as one that displays the appropriate RE pattern and/or PCR pattern. Plasmids identified through this procedure can be further evaluated using standard DNA sequencing procedures, as described above.

*Escherichia coli* strain Sable2$^R$ was purchased from Life Technologies (Bethesda, Md.) and served as initial host of the recombinant plasmids described in the examples below. Recombinant plasmids were introduced into *E. coli* strain Stable2$^R$ by electroporation using a Gene Pulser (BioRad Laboratories, Hercules, Calif.) set at 200Ω, 25 μF and 2.5 kV, as described (Ausubel et al, supra).

Bacterial strains were grown on tryptic soy agar (Difco, Detroit Mich.) or in tryptic soy broth (Difco, Detroit Mich.), which were made according to the manufacturer's directions. Unless stated otherwise, all bacteria were grown at 37° C. When appropriate, the media were supplemented with 100-μg/ml ampicillin (Sigma, St. Louis, Mo.). Bacterial strains were stored at −80° C. suspended in tryptic soy broth (Difco) containing 30% (v/v) glycerol (v/v; Sigma, St Louis Mo.) at ca. $10^9$ colony-forming units (herein referred to as "cfu") per ml.

EXAMPLE 2

Construction of a Prototype HIV-1 gp120 rdsRP Nucleocapsid

A functional eukaryotic translation expression cassette is obtained by incorporating an IRES that is functionally linked to the immunogen, the latter being placed immediately downstream of the IRES. Expression vector, designated "prϕ8Seg-S", carries the ϕ-8 segment-S pac sequence and gene-8, a positive selection allele, the encephalomyocarditis virus IRES [48], multiple cloning sites, a polyadenylation sequence and ϕ-8 segment-S 3'-prime RNA-dependent RNA polymerase recognition sequence, as shown (FIG. 5). The blunt-end MscI site serves as an insertion point for any desired gene, such as those outlined in the detailed description of this invention above. Note that genes 5, 9 and 12 are omit in the resultant rdsRP, as these genes are not required for nucleocapsid production [15,20]. In addition, φ-8 segment-M is not utilizes, as it is not required for nucleocapsid production and maintenance [15,20].

The components of plasmid prφ8Seg-S are assembled by joining the sequences obtained from the following sources:

1. The φ-8 segment-S pac sequence and gene-8 ([15]; Genbank accession # AF226853) are obtained by PCR from plasmid pLM2755 (kindly provided by Dr. Leonard Mindich, Department of Microbiology, Public Health Research Institute, NY, N.Y.).
2. A PSA encoding the *Escherichia coli* asd allele (Genbank accession no. V00262) for maintenance of the recombinant segment-S in the resultant rdsRP during propagation in *Escherichia coli* [15] is obtained by PCR from plasmid pYA292 [49].
3. The encephalomyocarditis virus IRES is obtained from pCITE4a by PCR, as described [50,51]. The 3-prime primer for this amplification encodes oning sites including MscI, EcoRI, SalI and NotI restriction endonuclease (RE) sites 3-prime to the IRES sequence (MscI is a blunt-end RE and provides an ATG start codon that is functionally linked to the IRES) and the bovine poly-adenylation sequence (obtained from pcDNA3.1 (Invitrogen)).
4. Similarly, the φ-8 segment-S RNA-dependent RNA polymerase recognition sequence is amplified from pLM2755 [15] by PCR.

The rdsRP is assembled using a sequential assembly procedure similar to the procedure used to assemble synthetic genes [52]. Thus, PCR-generated φ-8 segment-S pac sequence and gene-8 fragment is joined by T4 DNA ligase to the PCR-generated *E. coli* asd allele. This fusion fragment is amplified by PCR using primers specific for the 5-prime and 3-prime ends. Similarly, the PCR-generated encephalomyocarditis virus IRES::RE sites::poly-A fragment is joined by T4 DNA ligase to the PCR-generated φ-8 segment-S RNA-dependent RNA polymerase recognition sequence and the resultant fusion fragment is amplified by PCR using primers specific for the 5-prime and 3-prime ends of the fusion fragment. The two fusion fragments are then joined by ligation and amplified by PCR as above. This fragment is then inserted into the SmaI site in broad host range expression vector pBAD (Invitrogen, Carlsbad Calif.), which places the expression of the recombinant segment-S under the tight control of the L-arabinose-inducible *E. coli* araBAD promoter ($P_{BAD}$). The resultant plasmid, designated "prφ8Seg-S" is isolated and purified as described in Example 1.

An rdsRP capable of expressing HIV-1 gp120 in mammalian cells is constructed as follows. The sequence encoding syngp120 is obtained from pOGL1 by PCR so that MscI and NotI sites are created at the 5-prime and 3-prime ends of syngp120, respectively, as before [39]. The PCR-generated MscI::syngp120::NotI fragment is digested with MscI (New England Biolabs) and NotI (New England Biolabs) and inserted using T4 DNA ligase (New England Biolabs) into MscI-, NotI-digested prφ8Seg-S, as shown (FIG. 5); this procedure functionally links syngp120 to the IRES. The resultant plasmid is designated prdsRP-1 and rdsRP that incorporate the recombinant segment-S expressed by prdsRP-1 (Example 7) bear the capacity to express gp120 in mammalians cells.

EXAMPLE 3

Construction of a rdsRP that Expresses a Conformationally Constrained HIV-1 Envelope Immunogen and Induces Broadly Neutralizing Antibodies to HIV-1

The advent of conformationally constrained HIV-1 envelope (Env) immunogens (i.e gp120-CD4 fusions herein referred to as "FLSC" [53] that induce antibodies capable of neutralizing a broad cross-section of primary HIV-1 isolates made it feasible to develop HIV-1 vaccination strategies that afford protection through humoral mechanisms. Therefore, a second-generation rdsRP vector is constructed by inserting sequences encoding FLSC [53] in place of syngp120 using procedures described in examples 1 and 2; the resultant rdsRP is designated "rdsRP-FLSC".

It is important to note that there is direct evidence linking humoral immune mechanisms to the prevention and control of HIV-1. In particular, data demonstrating that monoclonal and polyclonal neutralizing antibodies against HIV-1 or SIV transfer protection against homologous challenge in animal models established direct evidence for protection through a humoral mechanism [54–65]. Nevertheless, reports describing the tertiary models of gp120 suggest that conserved epitopes exposed after binding to CD4, which are pivotal targets of broadly neutralizing antibodies, lie concealed within the core structure of unbound gp120. As a result, these key epitopes are poorly immunogenic in conventional Env, gp140 and gp120 subunit vaccines, which induce antibodies primarily to surface-exposed epitopes [66–72]. However, CD4-bound, conformationally constrained gp120 immunogens, such as FLSC [66–70] expose cryptic epitopes in gp120 that are normally only exposed following viral attachment to CD4 [66–70]. The availability of chemically and genetically stabilized conformationally constrained HIV-1 envelope (Env) immunogens (i.e FLSC), therefore, made it feasible to induce antibodies similar to those used in the above cited infusion studies that afford protection against HIV-1 [66–70]. Taken together, these observations indicate that immunization with rdsRP-FLSC has the potential to induce neutralizing antibodies against primary isolates of HIV-1 and provide protection against HIV-1 infection in humans.

EXAMPLE 4

Construction of an *Anthrax* rdsRP Vaccine

A functional eukaryotic translation expression cassette is obtained by incorporating an IRES that is functionally linked to the N-terminal region (i.e. amino acids 10 to 254) of *Bacillus anthrax* lethal factor (herein designated "tLF") by placing sequences encoding this immunogen downstream of the IRES in expression vector prφ8Seg-S (Example 2). The sequence encoding tLF is obtained from pCLF4 ([73]; kindly provided by Dr. Darrell Galloway, Department of Micribiology, Ohio State University Ohio) by PCR so that MscI and NotI sites are created at the 5-prime and 3-prime ends, respectively (Example 1). The PCR-generated tLF fragment is digested with MscI (New England Biolabs) and NotI (New England Biolabs) and inserted, using T4 DNA ligase (New England Biolabs), into MscI-, NotI-digested prφ8Seg-S, thereby functionally linking tLF to the IRES. The resultant plasmid is designated prdsRP-tLF and rdsRP that incorporate the recombinant segment-S expressed by prdsRP-tLF (Example 7) bear the capacity to express this non-toxic *anthrax* immunogen in mammalians cells. A second, functional eukaryotic translation expression cassette is obtained by incorporating an IRES that is functionally linked to the N-terminal region (i.e. amino acids 175 to 735) of *Bacillus anthrax* protective antigen (herein designated "tPA") by placing sequences encoding this immunogen [73] downstream of the IRES in expression vector prϕ8Seg-S (Example 2). The sequence encoding tPA is obtained from pCPA ([73]; kindly provided by Dr. Darrell Galloway, Department of Micribiology, Ohio State University Ohio) by PCR so that MscI and NotI sites are created at the 5-prime and 3-prime ends, respectively (Example 1). The PCR-generated tPA fragment is digested with MscI (New England Biolabs) and NotI (New England Biolabs) and inserted, using T4 DNA ligase (New England Biolabs), into MscI-, NotI-digested prϕ8Seg-S, thereby functionally linking tPA to the IRES. The resultant plasmid is designated prdsRP-tPA and rdsRP that incorporate the recombinant segment-S expressed by prdsRP-tPA (Example 7) bear the capacity to express this *anthrax* immunogen in mammalians cells.

It is important to note that nucleic acid vaccines encoding tLF and tPA afforded protection in mice challenged intravenously with 5×50% lethal doses of *Bacillus anthrax* lethal toxin (PA plus LF) [73]. In this study, 100% of mice immunized with nucleic acid vaccine that expressed tLF alone, tPA alone, or the combination of both survived such a challenge, whereas all of the unvaccinated mice died [73]. Since neutralization of *Bacillus anthrax* toxin is a correlate of protection in humans, these results indicate that immunization with prdsRP-tLF and prdsRP-tPA alone or in combination has the potential to induce *Bacillus anthrax* neutralizing antibodies and provide protection against a lethal *Bacillus anthrax* toxin infection in humans.

EXAMPLE 5

Construction of a rdsRP that Expresses an Immunogen and an Adjuvant

As an additional parallel track, the immunogenicity of rdsRP-1 (Example 2) and rdsRP-2 (Example 6) can be enhanced significantly be including sequences that encode the catalytic domain of cholera toxin (herein referred to as "ctxA1"), which are incorporated into a recombinant segment-M in the rdsRP. To this end, a second PSA (i.e. the kanamycin-resistance gene herein designated "kan$^r$" from plasmid pUC18K1 [47] is inserted immediately downstream of the segment-M pac sequence, the latter being amplified from pLM2669, which encodes and expresses a full-length cDNA copy of ϕ-8 segment-M (kindly provided by Dr. Leonard Mindich). The CtxA1 gene functionally linked to the 53 bp hepatitis C virus IRES (Genebank accession no. 1KH6_A; [45,46]) is then inserted downstream of kan$^R$ by blunt-end ligation. The 53 bp hepatitis C virus IRES is made synthetically (Example 1). Downstream of the ctxA1 gene, DNA sequences encoding a poly-adenylation site (from pcDNA3.1$_{ZEO}$; See Example 1) and the 3-prime RNA-dependent RNA polymerase recognition sequence are included (the latter is amplified from pLM2669).

EXAMPLE 6

Introduction of an Alphavirus Amplicon into the rdsRP System

Figure 6:
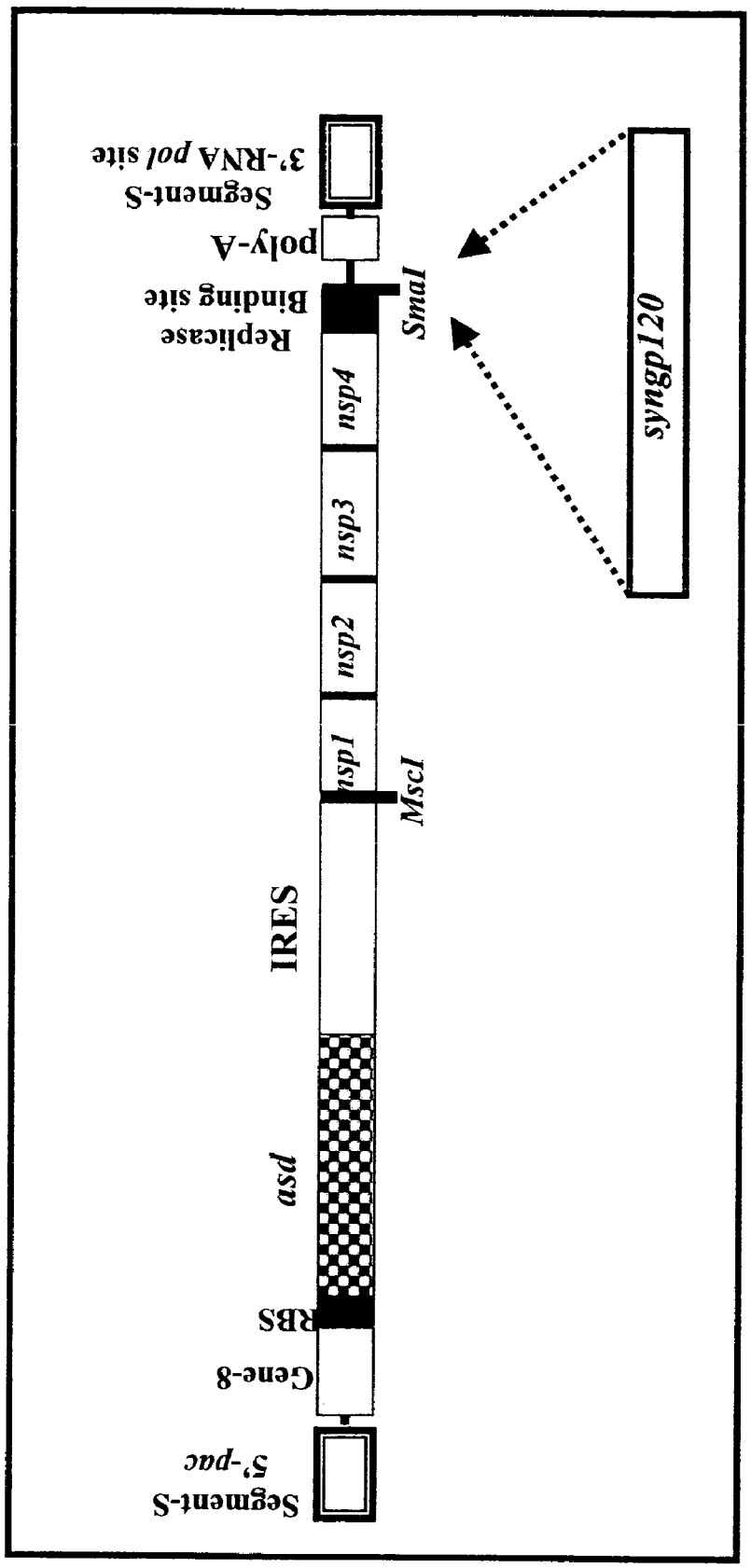

As noted above, rdsRP can harbor a mammalian translation expression cassette comprised of Semliki Forest virus (herein referred to as "SFV") self-amplifying replicon from plasmid pSFV1 (Invitrogen Inc., Carlsbad Calif.) functionally linked to syngp120 or to FLSC (See Examples 1 and 2). Genes encoding SFV non-structural proteins (herein referred to as "NSPs" 1–4 and the replicase recognition site in pSFV1 are amplified by PCR and inserted by blunt-end ligation into the MscI site immediately downstream and functionally linked to the IRES in prϕ8Seg-S (Example 2), resulting in prϕ8Ampl-S (FIG. 6). Incidentally, the SmaI RE site in plasmid prϕ8Ampl-S can serve as an insertion site for any desired gene, such as those outline above in the detailed description of the invention. In this instance, however, PCR-generated DNA encoding the syngp120 gene in pOGL1 (Example 1) is inserted into the SmaI site in prϕ8Ampl-S, which places it immediately downstream of, and functionally linked to, the SFV virus replicase recognition site (FIG. 6). RdsRP that harbor this recombinant segment-S are designated herein as rdsRP-2.

EXAMPLE 7

Generation, Isolation and Purification of rdsRP-1 and rdsRP-2

Batches of rdsRP-1 and rdsRP-2 are generated by replicating a parent dsRP on the bacterial transformant the carries the expression prdsRP-1 (i.e. expresses the 5'-pacS-gene-8::PBAD-Ωasd::IRES::syngp120::poly-A::3'-Seg-S recombinant segment-S; (wherein "::" indicates a novel nucleic acid junction; construction details are provided in Example 2) and prdsRP-2 (i.e. expresses the 5'-pacS-gene-8::P$_{BAD}$-Ωasd::IRES::SFV$_{nsp1-4}$::syngp120::poly-A::3'-Seg-S recombinant segment-S; Example 6), respectively (FIG. 4). Standard methods for incorporation of recombinant segments into dsRP and the subsequent replication, isolation and purification of the resultant rdsRP are used, as published in detail elsewhere [17,20,74,75] [14–16]. Briefly, rdsRP are generated in *Escherichia coli* strain JM109; recombinant plasmids prdsRP-1 and prdsRP-2 are introduced into *E. coli* Δasd mutant strain χ6212 by transformation [76] and ampicillin-resistant transformants are isolated on LBA containing 100 μg/ml ampicillin (Sigma).

The bacterial isolates are cultured at 37° C. for 24 hr; colonies that grow on the selective solid media are subsequently isolated and purified by standard methods [76]. To verify that the antibiotic-resistant isolates carrying the plasmid of interest, individual isolates are cultured in Luria-Bertani broth (LB; Difco, St Louis Mo.). The transformants are harvested after cultures reach an optical density at 600 nm (OD$_{600}$) of 0.9, relative to the OD$_{600}$ a sterile LB control. Plasmid DNA is isolated from these cultures and analyzed by RE digestion using those that generate a defined digestion pattern based on the predicted sequence of the recombinant plasmid, including EcoRI, PstI, HindIII, HaeI, SmaI, NotI, and SalI. In addition, the plasmids are screened by PCR using primers that amplify defined fragments within the recombinant segment-S including asd, IRES and syngp120. The PCR primers for the amplifications are designed as outlined in Example 1. The products of RE digestion and the PCR were analyzed by agarose gel electrophoresis [76]. A positive clone is defined as one that displays the appropriate RE pattern and PCR pattern. Plasmids identified through this procedure can be further evaluated using standard DNA sequencing procedures, as described (Example 1).

Finally, replication of parent dsRP ϕ-8 on χ6212 transformants that harbor the recombinant plasmids prdsRP-1 or pdsRP-3 generates the rdsRP designated rdsRP-1 and rdsRP-3, respectively. χ6212 carriers of rdsRP-1 and rdsRP-2 are isolated from within the resultant turbid plaques. These latter isolates are cultured on media lacking diaminopalmelic acid; under these circumstances only χ6212(rdsRP-1) and χ6212(rdsRP-2) carriers are capable of growth due to complementation of the lethal Δasd mutation by the expression of the recombinant segments in the rdsRPs. Methods for isolation and purification of rdsRP nucleocapsids, entailing liquid culture of carrier strain χ6212(rdsRP-1) and χ6212(rdsRP-2), osmotic lysis of the χ6212(rdsRP-1) and χ6212(rdsRP-2) bacilli and sucrose density gradient purification of the rdsRP-1 and rdsRP-2 nucleocapsids, have been published extensively in detail by others [14–17,20,74,75]. Residual endotoxin is removed by adsorption to End-X® Endotoxin Affinity Resin (Cape Cod Associates Inc, Cape Cod Mass.). The purified rdsRP are placed into Spectrapore 50,000 Da cutoff dialysis tubing and dialyzed in phosphate buffered saline (PBS) pH 7.3. The number of plaque-forming units (pfu) in the nucleocapsid preparations is measured by infecting χ6212 protoplasts with 10-fold serial dilutions of each preparation and plating this suspension in soft-agar, as described [20]. The nucleocapsid concentration is adjusted to $5 \times 10^{10}$ pfu/ml.

EXAMPLE 8

Infection of Human Dendritic Cells In Vitro with rdsRP

DsRP nucleocapsids have the unusual property of being able to auto-transform bacterial protoplasts, a process that requires gene-8 [20,77]. Since the mechanism of protoplast transfection resembles that of mammalian cells, rdsRP have the capacity to enter and express passenger immunogens in vitro following treatment of human monocyte-derived dendritic cells (MDDCs) with the purified rdsRP. In short, human PBMCs are separated from the blood of healthy donors by centrifugation in Histopaque 1077 (Sigma, St. Louis, Mo.). The cells are enriched for monocytes (90–95% pure) using the StemSep® Monocyte Enrichment Cocktail and a magnetic negative-selection column (StemSep, Vancouver, British Columbia). Following enrichment, the monocytes are plated in RPMI 1640 (Gibco-BRL, Grand Island, N.Y.) and incubated for 2 hours at 37° C. in a 5% $CO_2$ environment. Non-adherent cells and media are removed, and replaced with complete DC media, which comprises of RPMI 1640 supplemented with 10% fetal bovine serum (Gibco-BRL), 1% sodium pyruvate (Sigma), 1% non-essential amino acids (Gibco-BRL), Gentamycin (Gibco-BRL), 50 μM β-mecaptoethanal (Sigma), 10 μM Hepes (Sigma), 35 ng/ml interleukin-4 (IL-4, R&D Systems, Minnesota, Minn.), and 50 ng/ml granulocyte/monocyte-colony stimulating factor (GM-CSF, R&D Systems). The cells in such cultures develop the appearance and cell surface phenotype of immature MDDCs after 4 days in culture, as confirmed by microscopy and flow cytometry.

To evaluate the delivery and expression of gp120 encoded in rdsRP-1, MDDCs are treated with a range of doses (from $10^{3-10^7}$ pfu). Cells treated with the rdsRP vectors and the control cells are harvested after 24, 48 and 72 hr at 37° C. in 5% $CO_2$. The cells are washed twice with PBS and lysed in 1×SDS sample buffer and run on SDS-PAGE gels made with 5% to 15% gradients of polyacrylamide. The samples are run under non-reducing and reducing conditions to estimate the yields of oligomeric forms of gp160. The samples are transferred to PVDF membranes, which is probed with a mixture of monoclonal antibodies specific for defined epitopes of gp120 [66,78]. The extent of glycosylation of Env proteins is estimated by treatment with Endo-H prior to separation and evidence of glycosylation is taken as sine qua non that the gp120 RNA was expressed in the eukaryotic cell.

This experiment is designed to demonstrate that rdsRP-1 and rdsRP-2 bear an innate ability to enter mammalian cells and express gp120, wherein rdsRP-2 is capable of expressing significantly higher levels of gp120 that rdsRP-1 due to the incorporation of the SFV amplicon in rdsRP-2 (Example 6).

EXAMPLE 9

Immunogenicity of rdsRP Vaccine Vectors in Mice

Female BALB/c and C57B1/6 mice aged 6–8 weeks are obtained from Jackson Laboratories River (Bar Harbor, Me.). All mice are certified specific-pathogen free and upon arrival at the University of Maryland Biotechnology Institute Animal Facility are maintained in a microisolator environment and allowed to fee and drink ad lib.

The immunogenicity of rdsRP-1 (Example 2) and rdsRP-2 (Example 6) is assessed in groups of 10 mice, initially at dose of $10^9$ pfu. Both rdsRP-1 and rdsRP-2 are administered intragastrically three times spaced by 4-week intervals. In addition, a group of 10 mice is vaccinated intranasally with three $10^9$-pfu doses of rdsRP-1 and a second similar sized group of mice is vaccinated with rdsRP-2; in both instances the doses are spaced by 4-week intervals. In parallel, groups of 10 mice are vaccinated with a single $10^9$ pfu-dose of the rdsRP-1 or rdsRP-2, followed by two subcutaneous 50 μg-doses of soluble gp120 (or FLSC when appropriate). This enables the assessment of rdsRP-1 as a priming vaccine.

Fully glycosylated gp120 used in such boosts is purified from serum-free culture supernatants collected from 293 cells that are stably transfected with pOGL1 (Expresses $HIV-1_{MN}$ gp120) or pBaHu-120 (Expresses $HIV-1_{BaL1}$ gp120) and is supplied on a fee-for-service basis by the IHV μQuant core facility.

Additional groups of 10 mice are vaccinated intramuscularly with $10^3$ to $10^8$ rdsRP-1 or rdsRP-1 pfu (in 10-fold serial dilutions) suspended in endotoxin-free saline (0.85% (w/v) NaCl), by direct injection using a 30-gauge needle and a 1 ml tuberculin syringe. Booster vaccinations are given using the same formulation, route and dose as used to prime the mice, spaced by 4-week intervals.

The immune-priming properties of each construct is determined by sacrificing groups of 5 mice 28 days after vaccination and the numbers of gp120-specific antibody secreting and $CD4^+$ T cells are assessed as described in Example 10. The remaining 5 mice in each group are boosted as delineated above.

When rdsRP-1 and rdsRP-2 prove adept at delivering inducing humoral responses to the passenger immunogen, gp120, it will be possible to reduce the number of rdsRP-1 and rdsRP-2 dose. Thus, in the experimental protocol groups of 10 BALB/c mice that receive a single dose and two doses of each test rdsRP are included. These groups assess the effectiveness of both the prime and boosts in the extended three dose protocols.

When the boosts prove unnecessary, the immunogenicity of 3-fold serial dilutions of each rdsRP, from $1 \times 10^4$ to $1 \times 10^9$ pfu, are evaluated to determine whether the lower doses elicit immune responses to gp120 (See Example 10).

This series of vaccination experiments is designed to demonstrate that rdsRP-1 and rdsRP-2 bear an innate ability to induce immune responses to gp120 in mice vaccinated intragastrically, intranasally, and subcutaneously. Since rdsRP-2 is capable of expressing significantly higher levels of gp120 that rdsRP-1 due to the incorporation of the SFV amplicon in rdsRP-2 (Example 6), the immune responses in mice vaccinated with rdsRP-2 are generally stronger in magnitude.

EXAMPLE 10

Measurement of Immune Responses

To measure serum IgG and IgA responses to gp120, sera are collected before and at 10-day intervals after vaccination. About 400–500 μl of blood is collected into individual tubes from the tail vein of each mouse and allowed to clot by incubating for 4 hr on ice. After centrifugation in a microfuge for 5 min, the sera are transferred to fresh tubes and stored at −80° C. Mucosal IgG and IgA responses to gp120 are determined using fecal pellets and vaginal washes that are harvested before and 10-day intervals after vaccination [79,80].

Standard ELISAs are used to quantitate the IgG and IgA responses to gp120 in the sera and mucosal samples [78,81], and conducted as a fee-for-service by the IHV's Viral Immunology Core facility. Fully glycosylated gp120 for the ELISA assays is purified as described (Example 9). The purified gp120 is suspended in PBS at a concentration of 3–10 μg/ml and will be used to coat 96-well ELISA plates. Ovalbumin is included in each ELISA as a negative control antigen and purified rdsRP nucleocapsids are included as a control antigen for vector immunogenicity. In addition, each ELISA also includes a positive control serum, fecal pellet or vaginal wash sample, when appropriate. The positive control samples are harvested from mice vaccinated intranasally with 10 μg gp120 mixed with 10 μg cholera toxin, as described [82]. The end-point titers are calculated by taking the inverse of the last serum dilution that produced an increase in the absorbance at 490 nm that is greater than the mean of the negative control row plus three standard error values.

When a vaccine construct induces high-titer serum IgG and IgA responses, the gp120-specific IgG and IgA responses are also measured in the mucosal compartment. Serum dimeric IgA is transported across mucosal surfaces in mice and it is difficult to distinguish between locally produced IgA and systemically produced serum IgA in the mucosal secretions. Therefore, a more direct measure of mucosal humoral immunity to gp120 is obtained by harvesting lamina propria lymphocytes from small intestinal, colonic and vaginal tissue 40 and 80 days after vaccination, using procedures that preserve lymphocyte function [38,83]. IgA-specific ELISPOT assays are conducted as described previously by our group previously [38,83] and the results are expressed as the number of gp120-specific IgA-producing cells per 10,000 IgA-producing cells [38].

When measuring the primary $CD4^+$ T cell immune responses after the first vaccination, groups of 5 mice are sacrificed 28 days after immunization, and Peyer's patch, lamina propria (mucosal sites) and spleen (systemic site) cells are harvested using standard procedures [38,83]. Single cell suspensions of enriched $CD4^+$ T cells from these tissues are used immediately to measure the magnitude of the gp120-specific $CD4^+$ T cell responses by cytokine-specific ELISPOT assay [38]. Each sample is stimulated with three doses (0.1, 1.0 and 10) μg/ml of gp120 and the numbers of gp120-specific $CD4^+$ T cells are determined by cytokine-specific ELISPOT assays for IL-2, IL-4, IL-5, IL-6, IL-10 and IFN-γ production. All ELISPOT assays are conducted using commercially-available capture and detection mAbs (R&D Systems and Pharmingen), as described [84,85]. Each assay includes mitogen (Con A) and ovalbumin controls.

EXAMPLE 11

Vaccination Protocol Discrimination Criteria

As indicated in example 10, the magnitude of humoral and $CD4^+$ T cell responses to the selected HIV-1 immunogens in mice vaccinated intragastrically and intranasally with the experimental rdsRP constructs are measured by conventional ELISA and ELISPOT assays. Individual immune response parameters are evaluated quantitatively with the idea of characterizing the magnitude and duration of the host responses that are generated by each construct. In addition, all experimental values are measured in triplicate and standard statistical analyses are used when measuring and comparing the individual responses (including ANOVA and Student T tests). To ensure reproducibility, each experiment is performed a minimum of two times. When appropriate, the number of mice can be increase in individual groups if trends are observed but there is insufficient statistical power to resolve the differences. The following set of criteria was formulated to enable one to discriminate between the rdsRP vaccination protocols in example 9:

"Go" Criteria:

1. The location of the response: Preference is assigned to vaccination protocols that elicit gp120-specific humoral responses in both mucosal and systemic sites.
2. The magnitude of the responses: Preference is assigned to vaccination protocol that elicits the strongest gp120-specific antibody and/or antibody secreting cell responses.
3. The duration of the response: Preference is assigned to vaccines that elicit responses that remain significantly elevated for the longest period after vaccination.
4. The minimum effective dose: Preference is assigned to vaccination protocols that achieve the immune responses above with the minimum dose of rdsRP and the fewest doses.

"No-Go" Criteria:

1. Vaccination protocols that fail to immune responses to the passenger immunogen.
2. When pertinent (i.e. when FLSC immunogens are inserted into the rdsRP instead of gp120), vaccination protocols that fail to induce broadly neutralizing antibodies to primary HIV-1 isolates.

REFERENCES

1 Sinclair, J. F., Tzagoloff, A., Levine, D. & Mindich, L. Proteins of bacteriophage phi6. *J Virol* 1975, 16(3), 685–695.

2 McGraw, T., Mindich, L. & Frangione, B. Nucleotide sequence of the small double-stranded RNA segment of bacteriophage phi 6: novel mechanism of natural translational control. *J Virol* 1986, 58(1), 142–151.

3 Gottlieb, P., Metzger, S., Romantschuk, M. et al. Nucleotide sequence of the middle dsRNA segment of bacteriophage phi 6: placement of the genes of membrane-associated proteins. *Virology* 1988, 163(1), 183–190.

4 Mindich, L., Nemhauser, I., Gottlieb, P. et al. Nucleotide sequence of the large double-stranded RNA segment of bacteriophage phi 6: genes specifying the viral replicase and transcriptase. *J Virol* 1988, 62(4), 1180–1185.

5 Mindich, L. Precise packaging of the three genomic segments of the double-stranded-RNA bacteriophage phi6. *Microbiol. Mol. Biol. Rev.* 1999, 63(i), 149–160.

6 Van Etten, J. L., Vidaver, A. K., Koski, R. K. & Burnett, J. P. Base composition and hybridization studies of the three double-stranded RNA segments of bacteriophage phi 6. *J Virol* 1974, 13(6), 1254–1262.

7 Sands, J. A. & Lowlicht, R. A. Temporal origin of viral phospholipids of the enveloped bacteriophage phi 6. *Can J Microbiol* 1976, 22(2), 154–158.

8 Bamford, D. H. & Palva, E. T. Structure of the lipid-containing bacteriophage phi 6. Disruption by Triton X-100 treatment. *Biochim Biophys Acta* 1980, 601(2), 245–259.

9 Berger, H. & Kennedy, K. Physical measurements on the lipid-containing bacteriophage phi 6. *Biochim Biophys Acta* 1980, 633(1), 68–76.

10 Olkkonen, V. M. & Bamford, D. H. The nucleocapsid of the lipid-containing double-stranded RNA bacteriophage phi 6 contains a protein skeleton consisting of a single polypeptide species. *J Virol* 1987, 61(8), 2362–2367.

11 Mindich, L. Bacteriophage phi 6: a unique virus having a lipid-containing membrane and a genome composed of three dsRNA segments. *Adv Virus Res* 1988, 35, 137–176.

12 Johnson, M. D., 3rd & Mindich, L. Plasmid-directed assembly of the lipid-containing membrane of bacteriophage phi 6. *J Bacteriol* 1994, 176(13), 4124–4132.

13 Van Etten, J. L., Vidaver, A. K., Koski, R. K. & Semancik, J. S. RNA polymerase activity associated with bacteriophage phi 6. *J Virol* 1973, 12(3), 464–471.

14 Mindich, L., Qiao, X., Qiao, J., Onodera, S., Romantschuk, M. & Hoogstraten, D. Isolation of additional bacteriophages with genomes of segmented double-stranded RNA. *J Bacteriol* 1999, 181(15), 4505–4508.

15 Hoogstraten, D., Qiao, X., Sun, Y., Hu, A., Onodera, S. & Mindich, L. Characterization of phi8, a bacteriophage containing three double-stranded RNA genomic segments and distantly related to Phi6. *Virology* 2000, 272(1), 218–224.

16 Qiao, X., Qiao, J., Onodera, S. & Mindich, L. Characterization of phi 13, a bacteriophage related to phi 6 and containing three dsRNA genomic segments. *Virology* 2000, 275(1), 218–224.

17 Onodera, S., Olkkonen, V. M., Gottlieb, P. et al. Construction of a transducing virus from double-stranded RNA bacteriophage phi6: establishment of carrier states in host cells. *J Virol* 1992, 66(1), 190–196.

18 Onodera, S., Qiao, X., Qiao, J. & Mindich, L. Directed changes in the number of double-stranded RNA genomic segments in bacteriophage phi6. *Proc Natl Acad Sci USA* 1998, 95(7), 3920–3924.

19 Qiao, X., Qiao, J. & Mindich, L. An in vitro system for the investigation of heterologous RNA recombination. *Virology* 1997, 227(1), 103–110.

20 Olkkonen, V. M., Gottlieb, P., Strassman, J., Qiao, X. Y., Bamford, D. H. & Mindich, L. In vitro assembly of infectious nucleocapsids of bacteriophage phi 6: formation of a recombinant double-stranded RNA virus. *Proc. Natl. Acad. Sci.* 1990, 87(23), 9173–9177.

21 Gottlieb, P., Strassman, J., Qiao, X. Y., Frucht, A. & Mindich, L. In vitro replication, packaging, and transcription of the segmented double-stranded RNA genome of bacteriophage phi 6: studies with procapsids assembled from plasmid-encoded proteins. *J Bacteriol* 1990, 172 (10), 5774–5782.

22 Gottlieb, P., Strassman, J., Frucht, A., Qiao, X. Y. & Mindich, L. In vitro packaging of the bacteriophage phi 6 ssRNA genomic precursors. *Virology* 1991, 181(2), 589–594.

23 Gottlieb, P., Strassman, J., Qiao, X., Frilander, M., Frucht, A. & Mindich, L. In vitro packaging and replication of individual genomic segments of bacteriophage phi 6 RNA. *J Virol* 1992, 66(5), 2611–2616.

24 Qiao, X., Casini, G., Qiao, J. & Mindich, L. In vitro packaging of individual genomic segments of bacteriophage phi 6 RNA: serial dependence relationships. *J Virol* 1995, 69(5), 2926–2931.

25 Davis, N. L., Brown, K. W. & Johnston, R. E. A viral vaccine vector that expresses foreign genes in lymph nodes and protects against mucosal challenge. *J Virol* 1996, 70(6), 3781–3787.

26 Pushko, P., Parker, M., Ludwig, G. V., Davis, N. L., Johnston, R. E. & Smith, J. F. Replicon-helper systems from attenuated Venezuelan equine encephalitis virus: expression of heterologous genes in vitro and immunization against heterologous pathogens in vivo. *Virology* 1997, 239(2), 389–401.

27 Caley, I. J., Betts, M. R., Irlbeck, D. M. et al. Humoral, mucosal, and cellular immunity in response to a human immunodeficiency virus type 1 immunogen expressed by a Venezuelan equine encephalitis virus vaccine vector. *J Virol* 1997, 71(4), 3031–3038.

28 Balasuriya, U. B., Heidner, H. W., Davis, N. L. et al. Alphavirus replicon particles expressing the two major envelope proteins of equine arteritis virus induce high level protection against challenge with virulent virus in vaccinated horses. *Vaccine* 2002, 20(11–12), 1609–1617.

29 Zhou, X., Berglund, P., Rhodes, G., Parker, S. E., Jondal, M. & Liljestrom, P. Self-replicating Semliki Forest virus RNA as recombinant vaccine. *Vaccine* 1994, 12(16), 1510–1514.

30 Berglund, P., Fleeton, M. N., Smerdou, C. & Liljestrom, P. Immunization with recombinant Semliki Forest virus induces protection against influenza challenge in mice. *Vaccine* 1999, 17(5), 497–507.

31 Fleeton, M. N., Sheahan, B. J., Gould, E. A., Atkins, G. J. & Liljestrom, P. Recombinant Semliki Forest virus particles encoding the prME or NS1 proteins of louping ill virus protect mice from lethal challenge. *J Gen Virol* 1999, 80 (Pt 5), 1189–1198.

32 Phenix, K. V., Wark, K., Luke, C. J. et al. Recombinant Semliki Forest virus vector exhibits potential for avian virus vaccine development. *Vaccine* 2001, 19(23–24), 3116–3123.

33 Withoff, S., Glazenburg, K. L., van Veen, M. L. et al. Replication-defective recombinant Semliki Forest virus encoding GM-CSF as a vector system for rapid and facile generation of autologous human tumor cell vaccines. *Gene Ther* 2001, 8(2041), 1515–1523.

34 Brinster, C., Chen, M., Boucreux, D. et al. Hepatitis C virus non-structural protein 3-specific cellular immune responses following single or combined immunization with DNA or recombinant Semliki Forest virus particles. *J Gen Virol* 2002, 83(Pt 2), 369–381.

35 Dalemans, W., Delers, A., Delmelle, C. et al. Protection against homologous influenza challenge by genetic immunization with SFV-RNA encoding Flu-HA. *Ann NY Acad Sci* 1995, 772, 255–256.

36 Conry, R. M., LoBuglio, A. F., Wright, M. et al. Characterization of a messenger RNA polynucleotide vaccine vector. *Cancer Res* 1995, 55(7), 1397–1400.

37 Fouts, T. R., Lewis, G. K. & Hone, D. M. Construction and characterization of a *Salmonella typhi*-based human immunodeficiency virus type 1 vector vaccine. *Vaccine* 1995, 13(6), 561–569.

38 Wu, S., Pascual, D. W., Lewis, G. K. & Hone, D. M. Induction of mucosal and systemic responses against human immunodeficiency virus type 1 glycoprotein 120 in mice after oral immunization with a single dose of a Salmonella-HIV vector. *AIDS Res. Hum. Retrovir.* 1997, 13(14), 1187–1194.

39 Shata, M. T. & Hone, D. M. Vaccination of mice with a Shigella-gp120 DNA vaccine vector induces HIV-1 gp120-specific CD8+ T cells and antiviral protective immunity. *J. Virol.* 2001, 75(20), 9665–9670.

40 Shata, M. T., Lewis, G. K. & Hone, D. M. Human Immunodeficiency Virus-1 envelope-specific T cells elicited by oral vaccination with a *Salmonella*-gp160 DNA vaccine vector in mice. *Vaccine* 2001, 20, 623–629.

41 Haas, J., Park, E. C. & Seed, B. Codon usage limitation in the expression of HIV-1 envelope glycoprotein. *Curr Biol* 1996, 6(3), 315–324.

42 Andre, S., Seed, B., Eberle, J., Schraut, W., Bultmann, A. & Haas, J. Increased immune response elicited by DNA vaccination with a synthetic gp120 sequence with optimized codon usage. *J Virol* 1998, 72(2), 1497–1503.

43 Fouts, T. R., Tuskan, R., Godfrey, K. et al. Expression and characterization of a single-chain polypeptide analogue of the human immunodeficiency virus type 1 gp120-CD4 receptor complex. *J Virol* 2000, 74(24), 11427–11436.

44 Jang, S. K., Krausslich, H. G., Nicklin, M. J., Duke, G. M., Palmenberg, A. C. & Wimmer, E. A segment of the 5' nontranslated region of encephalomyocarditis virus RNA directs internal entry of ribosomes during in vitro translation. *J Virol* 1988, 62(8), 2636–2643.

45 Kieft, J. S., Zhou, K., Jubin, R., Murray, M. G., Lau, J. Y. & Doudna, J. A. The hepatitis C virus internal ribosome entry site adopts an ion-dependent tertiary fold. *J Mol Biol* 1999, 292(3), 513–529.

46 Kieft, J. S., Zhou, K., Grech, A., Jubin, R. & Doudna, J. A. Crystal structure of an RNA tertiary domain essential to HCV IRES-mediated translation initiation. *Nat Struct Biol* 2002, 9(5), 370–374.

47 Menard, R., Sansonetti, P. J. & Parsot, C. Nonpolar mutagenesis of the ipa genes defines IpaB, IpaC, and IpaD as effectors of *Shigella flexneri* entry into epithelial cells. *J Bacteriol* 1993, 175(18), 5899–5906.

48 Parks, G. D., Duke, G. M. & Palmenberg, A. C. Encephalomyocarditis virus 3C protease: efficient cell-free expression from clones which link viral 5' noncoding sequences to the P3 region. *J. Virol.* 1986, 60(2), 376–384.

49 Galan, J. E., Nakayama, K. & Curtiss, R. d. Cloning and characterization of the asd gene of *Salmonella typhimurium*: use in stable maintenance of recombinant plasmids in *Salmonella* vaccine strains. *Gene* 1990, 94(1), 29–35.

50 Bagley, K. C., Fouts, T. R., Carbonetti, N., DeVico, A. L., Lewis, G. K. & Hone, D. M. Immunogenicity of a dicistronic DNA vaccine that directs coincident expression of the 120 kDa glycoprotein of human immunodeficiency virus and the catalytic domain of cholera toxin. (Submitted). 2002.

51 Agwale, S. M., Shata, M. T., Reitz, M. S., Jr. et al. A Tat subunit vaccine confers protective immunity against the immune-modulating activity of the human immunodeficiency virus type-1 Tat protein in mice. *Proc Natl Acad Sci USA* 2002, 99(15), 10037–10041.

52 Haas, J., Park, E. C. & Seed, B. Codon usage limitation in the expression of HIV-1 envelope glycoprotein. *Curr. Biol.* 1996, 6(3), 315–324.

53 Fouts, T. R., Tuskan, R., Godfrey, K. et al. Expression and characterization of a single-chain polypeptide analogue of the human immunodeficiency virus type 1 gp120-CD4 receptor complex. *J. Virol.* 2000, 74(24), 11427–11436.

54 Emini, E. A., Nara, P. L., Schleif, W. A. et al. Antibody-mediated in vitro neutralization of human immunodeficiency virus type 1 abolishes infectivity for chimpanzees. *J. Virol.* 1990, 64(8), 3674–3678.

55 Putkonen, P., Thorstensson, R., Ghavamzadeh, L. et al. Prevention of HIV-2 and SIVsm infection by passive immunization in cynomolgus monkeys. *Nature* 1991, 352(6334), 436–438.

56 Emini, E. A., Schleif, W. A., Nunberg, J. H. et al. Prevention of HIV-1 infection in chimpanzees by gp120 V3 domain-specific monoclonal antibody. *Nature* 1992, 355(6362), 728–730.

57 Conley, A. J., Kessler, J. A., II, Boots, L. J. et al. The consequence of passive administration of an anti-human immunodeficiency virus type 1 neutralizing monoclonal antibody before challenge of chimpanzees with a primary virus isolate. *J. Virol.* 1996, 70(10), 6751–6758.

58 Haigwood, N. L., Watson, A., Sutton, W. F. et al. Passive immune globulin therapy in the SIV/macaque model: early intervention can alter disease profile. *Immunol. Lett.* 1996, 51(1–2), 107–114.

59 Prince, A. M., Reesink, H., Pascual, D. et al. Prevention of HIV infection by passive immunization with HIV immunoglobulin. *AIDS Res. Hum. Retrovir.* 1991, 7(12), 971–973.

60 Parren, P. W., Ditzel, H. J., Gulizia, R. J. et al. Protection against HIV-1 infection in hu-PBL-SCID mice by passive immunization with a neutralizing human monoclonal antibody against the gp120 CD4-binding site. *Aids* 1995, 9(6), F1–6.

61 Murthy, K. K., Cobb, E. K., Rouse, S. R., Lunceford, S. M., Johnson, D. E. & Galvan, A. R. Correlates of protective immunity against HIV-1 infection in immunized chimpanzees. *Immunol. Lett.* 1996, 51(1–2), 121–124.

62 Mascola, J. R., Lewis, M. G., Stiegler, G. et al. Protection of Macaques against pathogenic simian/human immunodeficiency virus 89.6PD by passive transfer of neutralizing antibodies. *J. Virol.* 1999, 73(5), 4009–4018.

63 Mascola, J. R., Stiegler, G., VanCott, T. C. et al. Protection of macaques against vaginal transmission of a pathogenic HIV-1/SIV chimeric virus by passive infusion of neutralizing antibodies. *Nat. Med.* 2000, 6(2), 207–210.

64 Baba, T. W., Liska, V., Hofmann-Lehmann, R. et al. Human neutralizing monoclonal antibodies of the IgG1 subtype protect against mucosal simian-human immunodeficiency virus infection. *Nat. Med.* 2000, 6(2), 200–206.

65 Hofmann-Lehmann, R., Vlasak, J., Rasmussen, R. A. et al. Postnatal passive immunization of neonatal macaques with a triple combination of human monoclonal antibodies against oral simian-human immunodeficiency virus challenge. *J. Virol.* 2001, 75(16), 7470–7480.

66 Moore, J. P., Willey, R. L., Lewis, G.K., Robinson, J. & Sodroski, J. Immunological evidence for interactions between the first, second, and fifth conserved domains of the gp120 surface glycoprotein of human immunodeficiency virus type 1. *J. Virol.* 1994, 68(11), 6836–6847.

67 Moore, J. P., Thali, M., Jameson, B. A. et al. Immunochemical analysis of the gp120 surface glycoprotein of human immunodeficiency virus type 1: probing the structure of the C4 and V4 domains and the interaction of the C4 domain with the V3 loop. *J. Virol.* 1993, 67(8), 4785–4796.

68 Kang, C. Y., Hariharan, K., Nara, P. L., Sodroski, J. & Moore, J. P. Immunization with a soluble CD4-gp120 complex preferentially induces neutralizing anti-human immunodeficiency virus type 1 antibodies directed to conformation-dependent epitopes of gp120. *J. Virol.* 1994, 68(9), 5854–5862.

69 DeVico, A. L., Rahman, R., Welch, J. et al. Monoclonal antibodies raised against covalently crosslinked complexes of human immunodeficiency virus type 1 gp120 and CD4 receptor identify a novel complex-dependent epitope on gp120. *Virol.* 1995, 211(2), 583–588.

70 Pal, R., DeVico, A., Rittenhouse, S. & Samgadharan, M. G. Conformational perturbation of the envelope glycoprotein gp120 of human immunodeficiency virus type 1 by soluble CD4 and the lectin succinyl Con A. *Virology* 1993, 194(2), 833–837.

71 Sullivan, N., Sun, Y., Sattentau, Q. et al. CD4-Induced conformational changes in the human immunodeficiency virus type 1 gp120 glycoprotein: consequences for virus entry and neutralization. *J. Virol.* 1998, 72(6), 4694–4703.

72 LaCasse, R. A., Follis, K. E., Trahey, M., Scarborough, J. D., Littman, D. R. & Nunberg, J. H. Fusion-competent vaccines: broad neutralization of primary isolates of HIV. *Science* 1999, 283(5400), 357–362.

73 Price, B. M., Liner, A. L., Park, S., Leppla, S. H., Mateczun, A. & Galloway, D. R. Protection against *anthrax* lethal toxin challenge by genetic immunization with a plasmid encoding the lethal factor protein. *Infect. Immun.* 2001, 69(7), 4509–4515.

74 Mindich, L., Qiao, X., Onodera, S., Gottlieb, P. & Strassman, J. Heterologous recombination in the double-stranded RNA bacteriophage phi 6. *J Virol* 1992, 66(5), 2605–2610.

75 Mindich, L., Qiao, X. & Qiao, J. Packaging of multiple copies of reduced-size genomic segments by bacteriophage phi 6. *Virology* 1995, 212(1), 213–217.

76 Ausubel, F. M., Brent, R., Kingston, R. E. et al. *Current protocols in Immunology.*, Greene Publishing Associates and Wiley-Intersciences, John Wiley and Sons., New York, N.Y., 1992. Chapter 11, Pp11.12.11–11.12.13.

77 Kakitani, H., Iba, H. & Okada, Y. Penetration and partial uncoating of bacteriophage phi 6 particle. *Virol.* 1980, 101(2), 475–483.

78 Abacioglu, Y. H., Fouts, T. R., Laman, J. D. et al. Epitope mapping and topology of baculovirus-expressed HIV-1 gp160 determined with a panel of murine monoclonal antibodies. *AIDS Res. Hum. Retrovir.* 1994, 10(4), 371–381.

79 Srinivasan, J., Tinge, S., Wright, R., Herr, J. C. & Curtiss, R., 3rd. Oral immunization with attenuated *Salmonella* expressing human sperm antigen induces antibodies in serum and the reproductive tract. *Biol. Reprod.* 1995, 53(2), 462–471.

80 Staats, H. F., Nichols, W. G. & Palker, T. J. Mucosal immunity to HIV-1: systemic and vaginal antibody responses after intranasal immunization with the HIV-1 C4/V3 peptide TISPIO MN(A). *J. Immunol.* 1996, 157 (1), 462–472.

81 Pincus, S. H., Wehrly, K., Cole, R. et al. In vitro effects of anti-HIV immunotoxins directed against multiple epitopes on HIV type 1 envelope glycoprotein 160. *AIDS Res. Hum. Retrovir.* 1996, 12(11), 1041–1051.

82 Yamamoto, S., Kiyono, H., Yamamoto, M. et al. A nontoxic mutant of cholera toxin elicits Th2-type responses for enhanced mucosal immunity. *Proc. Natl. Acad. Sci.* 1997, 94(10), 5267–5272.

83 Wu, S., Pascual, D. W., VanCott, J. L. et al. Immune responses to novel *Escherichia coli* and *Salmonella typhimurium* vectors that express colonization factor antigen I (CFA/I) of enterotoxigenic *E. coli* in the absence of the CFA/I positive regulator cfaR. *Infect. Immun.* 1995, 63(12), 4933–4938.

84 Xu-Amano, J., Kiyono, H., Jackson, R. J. et al. Helper T cell subsets for immunoglobulin A responses: oral immunization with tetanus toxoid and cholera toxin as adjuvant selectively induces Th2 cells in mucosa associated tissues. *J. Exp. Med.* 1993, 178(4), 1309–1320.

85 Okahashi, N., Yamamoto, M., Vancott, J. L. et al. Oral immunization of interleukin-4 (IL-4) knockout mice with a recombinant *Salmonella* strain or cholera toxin reveals that CD4+ Th2 cells producing IL-6 and IL-10 are associated with mucosal immunoglobulin A responses. *Infect. Immun.* 1996, 64(5), 1516–1525.

I claim:

1. A double stranded RNA (dsRNA) phage that expresses at least one genetic sequence in eukaryote cells, comprising:
    a cap independent translation enhancer (CITE); and
    at least one genetic sequence that is expressed in a eukaryote cell, wherein said CITE and said at least one genetic sequence are functionally linked and are incorporated into one or more dsRNA segments in the dsRNA.

2. The dsRNA phage of claim 1 wherein said at least one genetic sequence encodes a vaccine antigen.

3. The dsRNA phage of claim 1 wherein said at least one genetic sequence encodes a bioactive protein.

4. The dsRNA phage of claim 1 wherein said at least one genetic sequence encodes an immunoregulatory protein.

5. The dsRNA phage of claim 1 wherein said at least one genetic sequence encodes an antisense RNA.

6. The dsRNA phage of claim 1 wherein said at least one genetic sequence encodes a catalytic RNA.

7. The dsRNA phage of claim 1 wherein said at least one genetic sequence encodes an immunogen.

8. The dsRNA phage of claim 1 wherein said CITE and said at least one genetic sequence are incorporated into an L segment.

9. The dsRNA phage of claim 1 wherein said CITE and said at least one genetic sequence are incorporated into an M segment.

10. The dsRNA phage of claim 1 wherein said CITE and said at least one genetic sequence are incorporated into an S segment.

11. The dsRNA phage of claim 1 wherein at said at least one genetic sequence includes a sequence encoding for green fluorescent protein.

12. The dsRNA phage of claim 1 wherein said at least one genetic sequence encodes an immunogen and a cytokine.

13. The dsRNA phage of claim 1 further comprising an alpha-virus self-amplifying expression system.

14. The dsRNA phage of claim 7 wherein said immunogen is viral.

15. The dsRNA phage of claim 7 wherein said immunogen is bacterial.

16. The dsRNA phage of claim 7 wherein said immunogen is from a parasite.

17. The dsRNA phage of claim 7 wherein said immunogen is a therapeutic agent.

18. The dsRNA phage of claim 7 wherein said immunogen is an autoimmune antigen.

19. The dsRNA phage of claim 7 wherein said immunogen is a tumor antigen or tumor specific antigen.

20. The dsRNA phage of claim 13 wherein said alpha-virus self-amplifying expression system is based on semliki forest virus.

* * * * *